United States Patent
Gospodarowicz et al.

(10) Patent No.: US 6,677,301 B1
(45) Date of Patent: *Jan. 13, 2004

(54) TRUNCATED KERATINOCYTE GROWTH FACTOR (KGF) HAVING INCREASED BIOLOGICAL ACTIVITY

(75) Inventors: Denis J. Gospodarowicz, Lafayette, CA (US); Frank R. Masiarz, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/573,068

(22) Filed: May 16, 2000

Related U.S. Application Data

(63) Continuation of application No. 09/074,950, filed on May 8, 1998, now Pat. No. 6,074,848, which is a continuation of application No. 08/467,937, filed on Jun. 6, 1995, now Pat. No. 5,863,767, which is a division of application No. 08/410,941, filed on Mar. 27, 1995, now Pat. No. 5,677,278, which is a continuation of application No. 08/086,427, filed on Jun. 29, 1993, now abandoned.

(51) Int. Cl.[7] ............... C07K 14/48; C07K 14/435; C07K 14/00
(52) U.S. Cl. ............... 514/2; 514/12; 424/85.1; 530/350; 530/351
(58) Field of Search ............... 514/2, 12; 424/85.1; 530/350, 351

(56) References Cited

U.S. PATENT DOCUMENTS

| | | | |
|---|---|---|---|
| 5,194,596 A | * | 3/1993 | Tischer et al. |
| 5,350,836 A | * | 9/1994 | Kopchick et al. |
| 5,654,405 A | | 8/1997 | Rubin et al. |
| 5,665,870 A | | 9/1997 | Rubin et al. |
| 5,677,278 A | | 10/1997 | Gospodarowicz et al. |
| 5,707,805 A | | 1/1998 | Rubin et al. |
| 5,731,170 A | | 3/1998 | Rubin et al. |
| 5,741,642 A | | 4/1998 | Rubin et al. |
| 5,773,586 A | | 6/1998 | Gospodarowicz et al. |
| 5,814,605 A | | 9/1998 | Pierce et al. |
| 5,824,643 A | | 10/1998 | Pierce et al. |
| 5,843,883 A | | 12/1998 | Gospodarowicz et al. |
| 5,863,767 A | | 1/1999 | Gospodarowicz et al. |
| 5,965,530 A | | 10/1999 | Pierce et al. |
| 6,074,848 A | | 6/2000 | Gospodarowicz et al. |

FOREIGN PATENT DOCUMENTS

| | | |
|---|---|---|
| WO | WO 90/08771 | 8/1990 |
| WO | WO 96/11949 | 4/1996 |
| WO | WO 96/11951 | 4/1996 |

OTHER PUBLICATIONS

Benjamin et al., 1998, Development 125:1591–1598.*
Vukicevic et al., 1996, PNAS USA 93:9021–9026.*
Massague, 1987, Cell 49:437–438.*
Pilbeam et al., 1993, Bone 14:717–720.*
Ngo et al., 1994, The Protein Folding Problem and Tertary Structure Prediction, Merz et al., eds., Birkhauser, Boston, pp. 491–495.*
Wells, 1990, Biochemistry 29:8509–8517.*
Powers et al., 2000, Endocrine–Related Cancer 7:165–197.*
Bellosta et al., *J. Cell Biol. 121*(3):705–713 (1993).
Bowie et al. *Science 247*:1306–1310 (1990).
Finch et al., *Science 2*:752–755 (1989).
Ron et al. *J. Biol Chem.* 268(4):2984–2988.

* cited by examiner

*Primary Examiner*—Elizabeth Kemmerer
(74) *Attorney, Agent, or Firm*—Roberta L. Robins; Joseph H. Guth; Robert P. Blackburn

(57) ABSTRACT

The present invention relates to a keratinocyte growth factor fragment, $KGF_{des1-23}$, or an analog thereof that is composed of a portion of an amino acid sequence of mature, full length keratinocyte growth factor, $KGF_{163}$. The fragment exhibits at least a 2-fold increase in mitogenic activity as compared to a mature, recombinant keratinocyte growth factor, rKGF, but lacks a sequence comprising the first 23 amino acid residues. C-N-D-M-T-P-E-Q-M-A-T-N-V-N-C-S-S-P-E-R-H-T-R- (SEQ ID NO: 2) of the $KGF_{163}$ N-terminus. The present invention also relates to a DNA molecule encoding $KGF_{des1-23}$, an expression vector and a transformed host containing the DNA molecule, and a method of producing $KGF_{des1-23}$ by culturing the transformed host. The present invention further relates to a conjugate of $KGF_{des1-23}$ and a toxin molecule, and the use thereof for treatment of hyperproliferative disease of the epidermis. Moreover, the present invention relates to a therapeutic composition containing $KGF_{des1-23}$ and a pharmaceutically acceptable carrier and the use thereof for wound healing purposes.

2 Claims, 5 Drawing Sheets

|                                                Long Form Start                                       CHO Site
|                                                  1           5              10              15
| sequence    CYS-ASN-ASP-MET-THR-PRO-GLU-GLN-MET-ALA-THR-ASN-VAL-ASN-CYS- Short Form Start
             16              20                     25                 30
| sequence    SER-SER-PRO-GLU-ARG-HIS-THR-ARG-SER-TYR-ASP-TYR-MET-GLU-GLY- 31              35              40                      45
| sequence    GLY-ASP-ILE-ARG-VAL-ARG-ARG-LEU-PHE-CYS-ARG-THR-GLN-TRP-TYR- 46              50              55                      60
| sequence    LEU-ARG-ILE-ASP-LYS-ARG-GLY-LYS-VAL-LYS-GLY-THR-GLN-GLU-MET- 61              65              70                      75
| sequence    LYS-ASN-ASN-TYR-ASN-ILE-MET-GLU-ILE-ARG-THR-VAL-ALA-VAL-GLY- 76              80              85                      90
| sequence    ILE-VAL-ALA-ILE-LYS-GLY-VAL-GLU-SER-GLU-PHE-TYR-LEU-ALA-MET- 91              95              100                     105
| sequence    ASN-LYS-GLU-GLY-LYS-LEU-TYR-ALA-LYS-LYS-GLU-CYS-ASN-GLU-ASP- 106             110             115                     120
| sequence    CYS-ASN-PHE-LYS-GLU-LEU-ILE-LEU-GLU-ASN-HIS-TYR-ASN-THR-TYR- 121             125             130                     135
| sequence    ALA-SER-ALA-LYS-TRP-THR-HIS-ASN-GLY-GLY-GLU-MET-PHE-VAL-ALA- 136             140             145                     150
| sequence    LEU-ASN-GLN-LYS-GLY-ILE-PRO-VAL-ARG-GLY-LYS-LYS-THR-LYS-LYS- 151             155             160
| sequence    GLU-GLN-LYS-THR-ALA-HIS-PHE-LEU-PRO-MET-ALA-ILE-THR

Figure 1

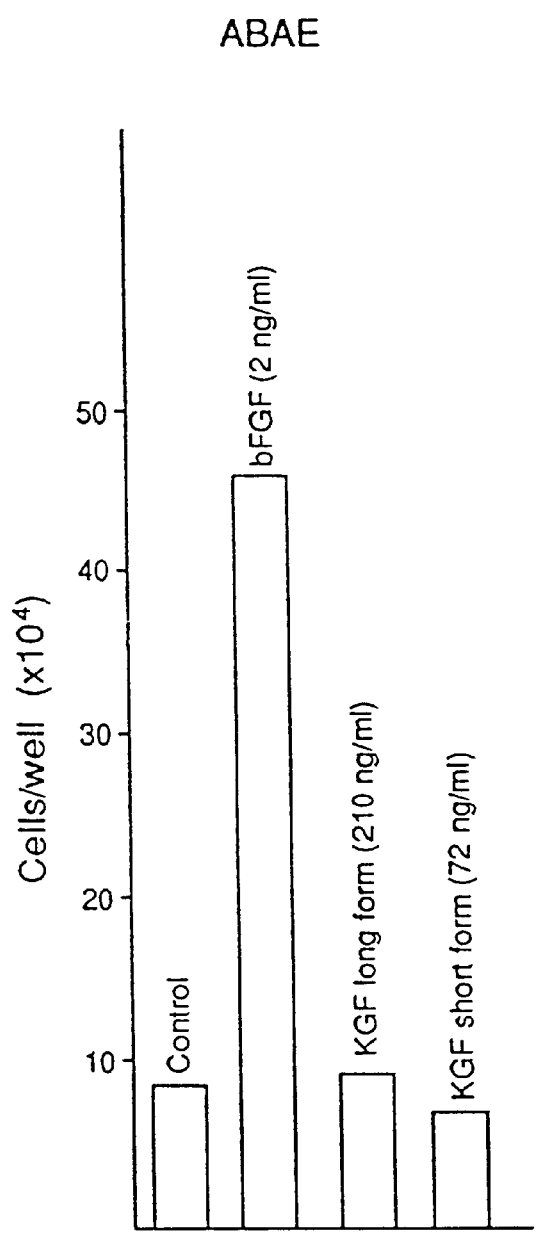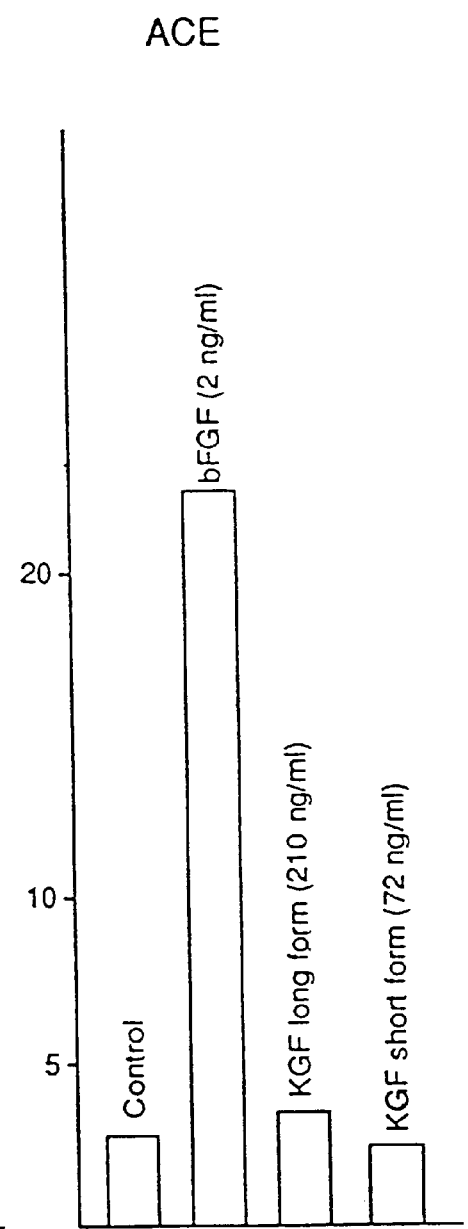
FIGURE 5A — ABAE
FIGURE 5B — ACE

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 194 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
                100                 105                 110

Val Glu Ser Glu Phe Tyr Leu Ala Met Asn Lys Glu Gly Lys Leu Tyr
                115                 120                 125

Ala Lys Lys Glu Cys Asn Glu Asp Cys Asn Phe Lys Glu Leu Ile Leu
            130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
                180                 185                 190

Ile Thr
```

(2) INFORMATION FOR SEQ ID NO: 2:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 2:

```
Cys Asn Asp Met Thr Pro Glu Gln Met Ala Thr Asn Val Asn Cys Ser
1               5                   10                  15
```

```
Ser Pro Glu Arg His Thr Arg
            20

(2) INFORMATION FOR SEQ ID NO: 3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Met His Lys Trp Ile Leu
1               5

(2) INFORMATION FOR SEQ ID NO: 4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

AGATCTCTGC AGCTATAATG CACAAATGGA TACTG                                  35

(2) INFORMATION FOR SEQ ID NO: 5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Thr Ile Ala Met Pro Leu Phe
1               5

(2) INFORMATION FOR SEQ ID NO: 6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

AGATCTGCGG CCGCTTAAGT TATTGCCATA GGAAGAAA                                38

(2) INFORMATION FOR SEQ ID NO: 7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO: 7:

Ser Tyr Asp Tyr Met Glu Gly Gly Asp Ile Arg Val Arg Arg Leu Phe
1               5                   10                  15

Xaa Arg Thr Gln
            20

(2) INFORMATION FOR SEQ ID NO: 8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GGTGGTGGAT CCCCAGCTTA GTTCATAGGT CC                                    32

(2) INFORMATION FOR SEQ ID NO: 9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

His Gln Asn Val Phe Arg Lys Ala Pro Ile Gln Ala
1               5                   10

(2) INFORMATION FOR SEQ ID NO: 10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GTGTTGGTTA ACGAATCGCT TAGCCGGAAT TTGTGC                                36

(2) INFORMATION FOR SEQ ID NO: 11:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Pro Ala Lys Arg Ser Tyr Asp Tyr Met Glu Gly Gly
1               5                   10

(2) INFORMATION FOR SEQ ID NO: 12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CCGCCGGCTA AGCGAAGTTA TGATTACATG GAAGGAGGG                                       39

(2) INFORMATION FOR SEQ ID NO: 13:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 13:

Thr Ile Ala Met Pro Leu Phe His
1               5

(2) INFORMATION FOR SEQ ID NO: 14:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 14:

GGTGGTGTCG ACTTAAGTTA TTGCCATAGG AAGAAAGTG                                       39

(2) INFORMATION FOR SEQ ID NO: 15:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 15:

GATCAGATCT AAATTTCCCG GATCC                                                      25

(2) INFORMATION FOR SEQ ID NO: 16:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 16:

TCTAGATTTA AAGGGCCTAG GAGCT                                                      25

(2) INFORMATION FOR SEQ ID NO: 17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: <Unknown>

-continued

```
        (xi) SEQUENCE DESCRIPTION: SEQ ID NO: 17:

Met Ser Tyr Asp Tyr Met Glu Gly Gly
1               5

(2) INFORMATION FOR SEQ ID NO: 18:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 18:

GTTGTTTCAT GAGTTATGAT TACATGGAAG GAGGG                              35

(2) INFORMATION FOR SEQ ID NO: 19:

(i) SEQUENCE CHARACTERISTICS:
         (A) LENGTH: 99 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: -
         (B) LOCATION: 13..14
         (D) OTHER INFORMATION: /note= "The figure did not contain
             the intervening polyhedrin sequences."

(xi) SEQUENCE DESCRIPTION: SEQ ID NO: 19:

TATAAATATT CCGGGCGCGG ATCGGTACCA GATCTGCAGA ATTCTAGAGG ATCCTGATCA    60

GCTAGCAGAG CTCGCGGCCG CCCGGGCCGT ACCGACTCT                          99
```

TRUNCATED KERATINOCYTE GROWTH FACTOR (KGF) HAVING INCREASED BIOLOGICAL ACTIVITY

This application is a continuation of U.S. patent application Ser. No. 09/074,950, filed May 8, 1998, now U.S. Pat. No. 6,074,848, which is a continuation of U.S. patent application Ser. No. 08/467,937, filed Jun. 6, 1995, now U.S. Pat. No. 5,863,767, which is a divisional of U.S. patent application Ser. No. 08/410,941, filed Mar. 27, 1995, now U.S. Pat. No. 5,677,278, which is a continuation of U.S. patent application Ser. No. 08/086,427, filed Jun. 29, 1993, now abandoned, from which applications priority is claimed pursuant to 35 U.S.C. § 120 and which applications are incorporated herein by reference in their entireties.

FIELD OF THE INVENTION

The present invention relates generally to keratinocyte growth factor ("KGF"). More specifically, this invention relates to a KGF fragment and analogs thereof having increased biological activity, and decreased cytotoxicity as compared to a mature, at recombinant, full length KGF expressed in an insect cell expression system. This KGF fragment lacks the first 23 amino acid residues of the N-terminus of mature, full-length KGF, including a potential glycosylation site. The N-terminus was previously believed to confer upon KGF its epithelial cell specificity.

KGF belongs to the family of fibroblast growth factors ("FGFs"), the prototype of which is represented by basic FGF ("bFGF"). KGF is, hence, also known as FGF-7. Like other FGFs, KGF is a heparin-binding protein, but unlike other FGFs, it has a unique target cell specificity. In particular, FGFs are generally capable of stimulating the proliferation and differentiation of a variety of cell types derived from the primary or secondary mesoderm as well as from neuroectoderm. KGF is similar to other FGFs in its ability to stimulate epithelial cell proliferation, but is dissimilar to other FGFs in its inability to stimulate endothelial cells or fibroblast proliferation, as discussed in Finch, P. W. et al., *Science* 245: 752–755 (1989). Mature, full-length KGF, designated herein as $KGF_{163}$, is a polypeptide with 163 amino acid residues, and possesses a potential N-glycosylation site at amino acid 14 of the consensus sequence for glycosylation that extends from amino acid residue 14 to 16 at the N-terminus, as indicated in Finch et al. (1989), loc. cit.

BACKGROUND OF THE INVENTION

FGFs, including acidic fibroblast growth factor ("aFGF") and basic fibroblast growth factor ("bFGF"), are known to have heparin-binding properties and have the ability to induce the differentiation and proliferation of ventral, as well as dorsal, mesoderm in early blastulae, as discussed in Gospodarowicz et al., *Cell. Biol. Rev.* 25:307–314 (1991), and Basilico et al., *Adv. Cancer Res.* 59:115–165 (1992). The response of cells to FGF is mediated through binding thereof to cell surface receptors known as fibroblast growth factor receptors ("FGFRs"), of which there are three inter-related types, as discussed in Hou et al., *Science* 251:665–668 (1991). High affinity FGFRs are tyrosine kinases and include the flg receptor ("FGFR-1"), the bek receptor ("FGFR-2"), and the K Sam receptor ("FGFR-3"), as discussed in Lee et al., *Science* 245:57–60 (1989); Dionne et al., *EMBO J*. 9:2685–2692 (1990); Miki et al., *Science* 251:72–75 (1991); Miki et al., *Proc. Natl. Acad. Sci. USA* 89:246–250 (1992); and Dell et al., *J. Biol. Chem.* 267:21225–21229, (1992).

Both FGFR-1 and FGFR-2 are widely expressed in mesodermal and neuroectodermal tissues, and both are able to bind aFGF and bFGF with similar affinities. FGFR-3, also referred to as KGFR, is a KGF receptor that is specific to epithelial cells. It is an alternative transcript of FGFR-2. In contrast to FGFR-2, which shows high affinity for both AFGF and bFGF and no affinity for KGF, FGFR-3 binds KGF and AFGF with an affinity approximately 20 to 1000 fold higher than bFGF, as discussed in Miki et al. (1992), and Dell et al. (1992), loc. cit.

The tightly restricted tissue distribution of KGFR to epithelial cells and, therefore, the tissue restricted activity of KGF, is desirable in many types of wound healing applications, as well as in the treatment of hyperproliferative diseases of the epidermis, such as psoriasis and basal cell carcinoma. Presently, except for KGF, no highly suitable factor exists for these applications. It would be desirable, therefore, if KGF could be modified to increase its potency and decrease its cytotoxicity for therapeutic applications.

Recently, Ron et al., *J. Biol. Chem.* 268:2984–2988 (February 1993) found that when $KGF_{163}$, was expressed in a prokaryotic expression system, a recombinant KGF ("rKGF") polypeptide could be obtained that possessed mitogenic activity. When the rKGF molecule was truncated by deletion of 3, 8, 27, 38, and 48 amino acid residues from the N-terminus of the mature $KGF_{163}$ polypeptide, biological activity of the resulting molecules varied. With deletion of 3 and 8 amino acid residues, respectively, the mitogenic activity of the resulting molecules did not appear to be affected as compared to full-length rKGF. Deletion of 27 amino acid residues, however, resulted in molecules that display 10–20 fold reduced mitogenic activity. Deletion of 38 and 48 amino acid residues, respectively, resulted in complete loss of mitogenic activity and heparin-binding ability. Ron et al., however, failed to produce any truncated rKGF fragments that possessed increased mitogenic activity as compared to the full-length rKGF molecule.

SUMMARY OF THE INVENTION

One of the objects of the present invention is to provide a KGF fragment or an analog thereof that contains a portion of the amino acid sequence of mature, full-length KGF and that exhibits at least a 2-fold, but preferably 7-fold, more preferably, a 7–10 fold increase in mitogenic activity as compared to the mature, full-length rKGF. This KGF fragment lacks a sequence comprising the first 23 N-terminal amino acid residues, C-N-D-M-T-P-E-Q-M-A-T-N-V-N-C-S-S-P-E-R-H-T-R- (SEQ ID NO: 2), of the mature, full-length rKGF.

Another one of the objects of the present invention is to provide a KGF fragment, as above, that has decreased cytotoxicity as compared to the mature, full-length rKGF.

Still another one of the objects of the present invention is to provide a conjugate that comprises the KGF fragment described above and a toxin molecule. The toxin molecule can be one of a ricin A molecule, a diphtheria toxin molecule, or a saporin molecule.

Yet another one of the objects of the present invention is to provide a therapeutic composition that contains the KGF fragment as described above and a pharmaceutically acceptable carrier, for example, one suitable for topical application to human skin.

Still another one of the objects of the present invention is to provide a DNA molecule that is composed of a nucleotide sequence that encodes the KGF fragment described above.

Yet another one of the objects of the present invention is to provide an expression vector that contains the DNA molecule that encodes the KGF fragment above and a regulatory sequence for expression of the DNA molecule. The expression vector can be, for example, a yeast, a bacterial, a mammalian or a baculovirus expression vector.

Yet another one of the objects of the present invention is to provide a host cell transformed with the expression vector described above. The host cell can be, for example, a prokaryote such as a bacterial cell, or a eukaryote such as a yeast cell, a mammalian cell, or an insect cell.

Yet another one of the objects of the present invention is to provide a method of producing the KGF fragment by culturing the transformed host cell as described above and isolating the KGF fragment from the culture.

Still another one of the objects of the present invention is to provide a method of stimulating epithelial cell growth by applying the KGF fragment to an area in which epithelial cell growth is desired and allowing the cells to grow.

Still another one of the objects of the present invention is to provide a method for wound healing by applying the therapeutic composition described above to an area of a wound to be treated and allowing the wound to heal.

Still another one of the objects of the present invention is to provide a method of treating a hyperproliferative disease of the epidermis by applying the conjugate described above to an area to be treated.

Further objects, features, and advantages of the present invention would be apparent to a person of ordinary skill in the art and need not be enumerated here.

SUMMARY OF THE DRAWINGS

FIG. 1 shows the amino acid sequence of the mature, full-length, human KGF polypeptide, beginning with the N-terminus and containing 163 amino acid residues, having a single consensus sequence for glycosylation at amino acid residues 14–16. The amino acid sequence of the mature KGF polypeptide corresponds to amino acid nos. 32 to 194 of SEQ ID NO: 1.

FIGS. 5A and B compares the biological activity of the long, i.e., full-length rKGF, and the short, i.e., rKGF$_{des1-23}$, form of KGF versus bFGF on vascular endothelial cells derived from large vessels (A:ABAE cells) or capillary cells (B:ACE cells).

DETAILED DESCRIPTION OF THE PREFERRED EMBODIMENTS

Figure 2:
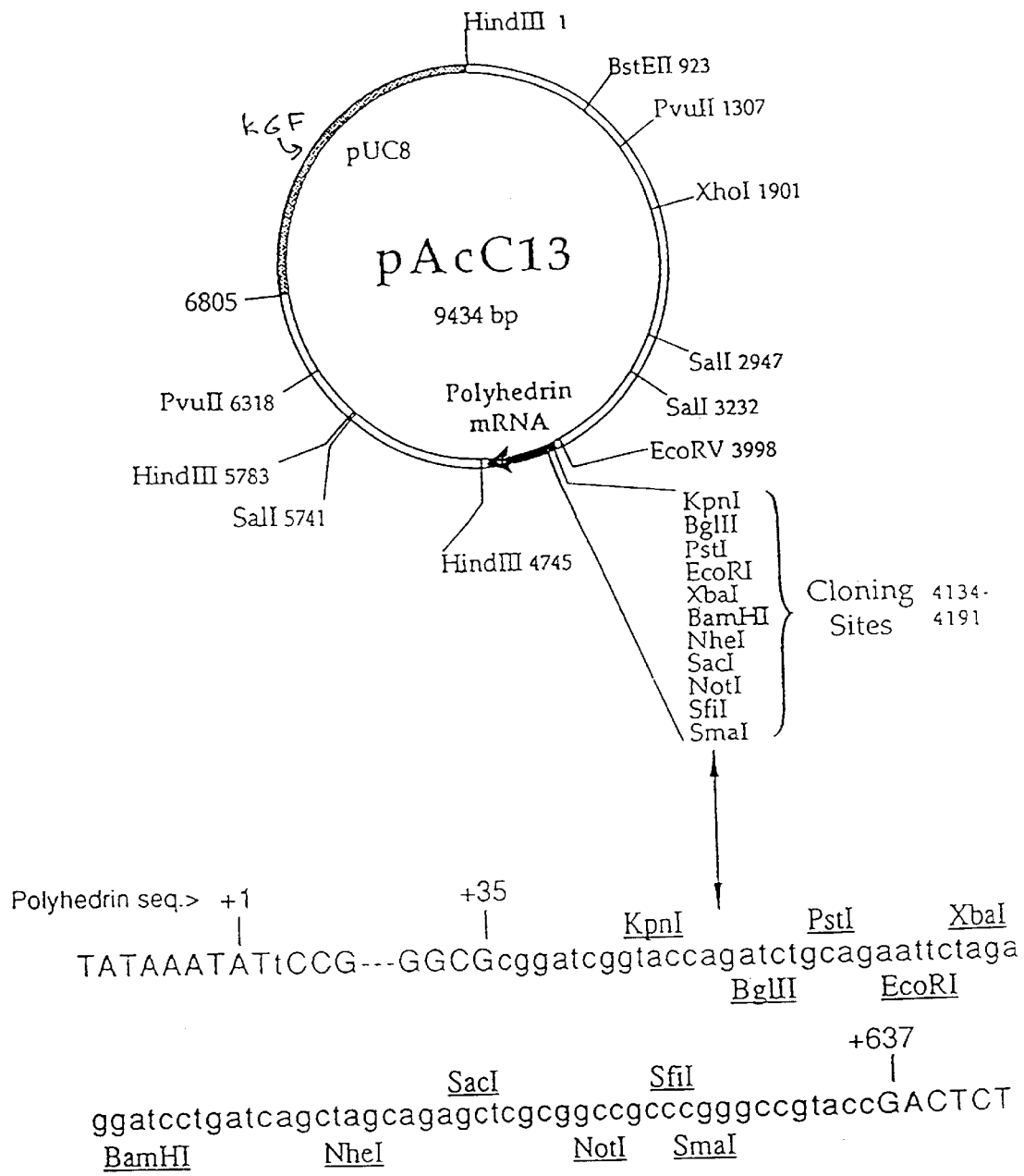
FIG. 2 shows the pAcC13 expression vector into which the 163 amino acid sequence of KGF has been inserted. The polylinker and flanking sequences shown in FIG. 2 are referred as SEQ ID NO: 19 in the Sequence Listing.
Figures 3A, 3B:
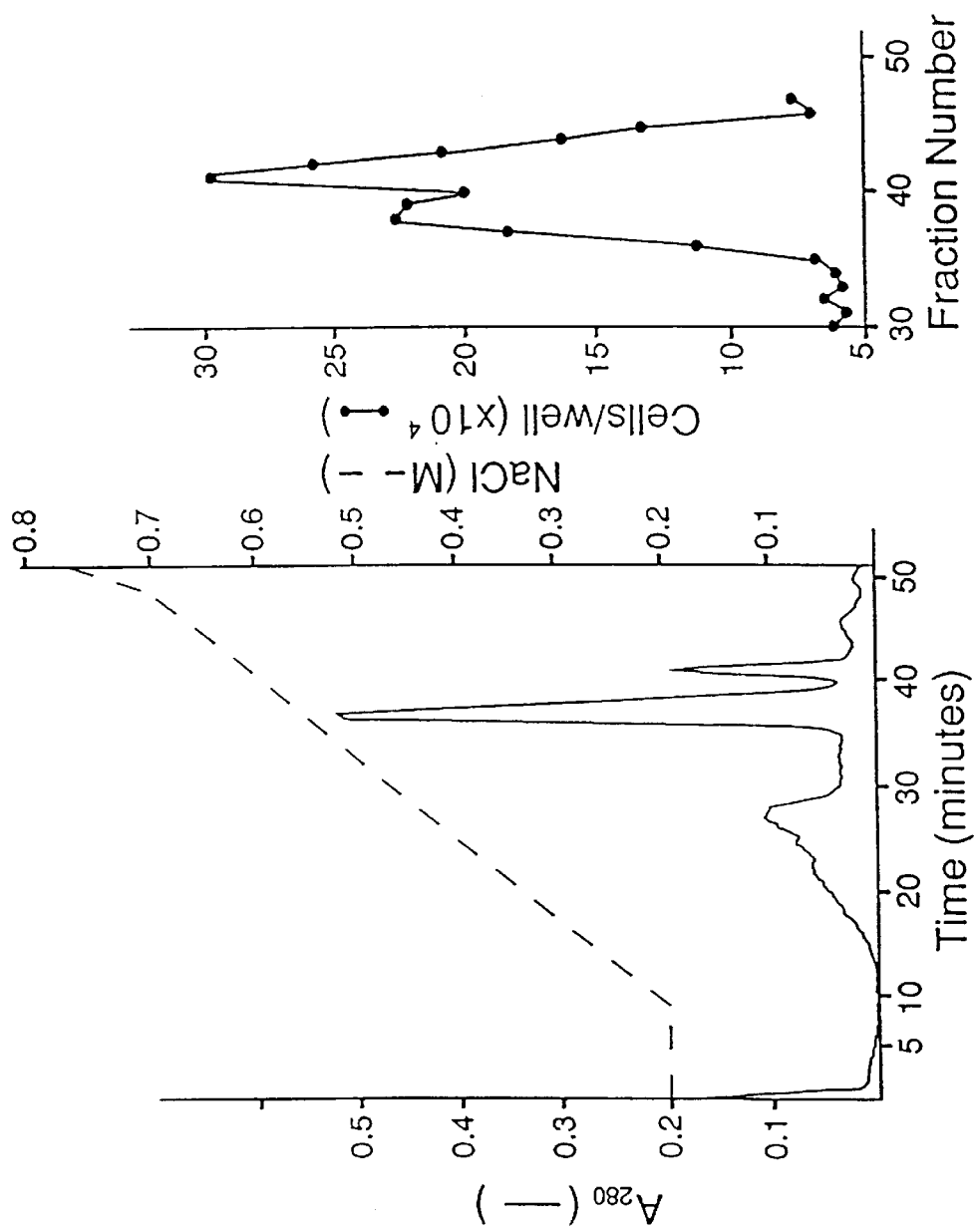
FIGS. 3A and B illustrates the protein elution profile (A) and bioactivity profile (B) of the rKGF obtained from a Mono S HR5/5 cation exchange FPLC column.

It has been surprisingly discovered that a truncated, unglycosylated KGF having a deletion spanning the first 23 N-terminal amino acid residues of mature recombinant KGF ("rKGF"), herein designated the KGF fragment or KGF$_{des1-23}$, possesses a much greater biological activity and decreased cytotoxicity on epithellal cells as compared with the mature, full-length rKGF. Generally, the KGF fragment of the present invention retains the specificity of KGF for stimulation of epithellal cell proliferation.

The following definitions are incorporated herein and are provided for a better understanding of the present invention.

Definitions

As used herein, the term "keratinocyte growth factor" or "KGF" refers to a ember of a group of structurally distinct proteins known as FGFs that display varying degrees of sequence homology, suggesting that they are encoded by a related family of genes. The FGFs share common receptor sites on cell surfaces. KGF, for example, can bind to FGFR-3.

"Mature, full-length KGF" or "long form of KGF" or "KGF$_{163}$," as used herein refers to the mature polypeptide that contains 163 amino acid residues, as shown in FIG. 1, and represented by amino acid residues 32 to 194 in SEQ ID NO: 1.

As used herein, "the KGF fragment" or "short form of KGF" or "KGF$_{des1-23}$ " refers to a polypeptide that is a truncated version of KGF$_{163}$, lacking the first 23 amino acid residues at the N-terminus of KGF$_{163}$. The sequence of the 23 deleted amino acid residues is shown in SEQ ID NO: 2. The properties of the KGF fragment include (i) its biological activity such as at least a 2-fold, preferably, a 7-fold and, more preferably, a 7–10 fold increase in stimulation of epithelial cell proliferation as compared to the rKGF$_{163}$ molecule, and (ii) its ability to bind to FGFR-3. The biological activity of the KGF fragment can be measured, for example, by the Balb/Mk cell proliferation assay, described in Example 5, section C.

An "analog of KGF$_{163}$" or "analog of the KGF fragment" herein refers to amino acid insertions, deletions, or substitutions in the relevant molecule that do not substantially affect its properties. The KGF$_{des1-23}$ analog herein retains at least the 2-fold increase, preferably, the 7-fold increase, more preferably, the 7–10 fold increase in mitogenic activity as compared to that of rKGF$_{163}$. For example, the analog herein can include conservative amino acid substitutions in the rKGF$_{des1-23}$ molecule.

"Conservative amino acid substitutions" herein are, for example, those that take place within a family of amino acids that are related in their side chains. The families of amino acids include (1) acidic, aspartic acid, glutamic acid; (2) basic: lysine, arginine, histidine; (3) non-polar: alanine, valine, leucine, isoleucine, proline, phenylalanine, inethionine, tryptophan; and (4) uncharged polar: glycine, asparagine, glutamine, cysteine, serine, threonine, tyrosine. Phenylalanine, tryptophan, and tyrosine are sometimes classified jointly as a family of aromatic amino acids. In particular, it is generally accepted that an isolated replacement of a leucine with an isoleucine or valine, or an aspartic acid with a glutamic acid, or a threonine with a serine, or a similar conservative substitutions of an amino acid with a structurally related amino acid, in an area outside of the polypeptide's active site will not have a major effect on the properties of the polypeptide.

The term "recombinant" as used herein in. relation to a polynucleotide intends a polynucleotide of semisynthetic, or synthetic origin, or encoded by cDNA or genomic DNA ("gDNA") such that (1) it is not associated with all or a portion of a polynucleotide with which it is associated in nature, (2) is linked to a polynucleotide other than that to which it is linked in nature, or (3) does not occur in nature.

A "expression vector" is a polynucleotide that is operable in a desired host cell and capable of causing the production of the KGF fragment. Examples of expression vectors are plasmids, integrating vectors, etc.

A "regulatory sequence" refers to a polynucleotide sequence that is necessary for regulation of expression of a coding sequence to which the polynucleotide sequence is operably linked. The nature of such regulatory sequences differs depending upon the host organism. In prokaryotes, such regulatory sequences generally include, for example, a promoter, and/or a transcription termination sequence. In eukaryotes, generally, such regulatory sequences include, for example, a promoter and/or a transcription termination sequence. The term "regulatory sequence" may also include additional components the presence of which are advantageous, for example, a secretory leader sequence for secretion of the polypeptide attached thereto.

"Operably linked" refers to a juxtaposition wherein the components so described are in a relationship permitting them to function in their intended manner. A regulatory sequence is "operably linked" to a coding sequence when it is joined in such a way that expression of the coding sequence is achieved under conditions compatible with the regulatory sequence.

A "coding sequence" is a polynucleotide sequence that is translated into a polypeptide, usually via mRNA, when placed under the control of an appropriate regulatory sequence. The boundaries of the coding sequence are generally determined by a translation start codon at its 5'-terminus and a translation stop codon at its 3'-terminus. A coding sequence can include, but is not limited to, cDNA, and recombinant polynucleotide sequences.

An "open reading frame" (ORF) is a region of a polynucleotide sequence that encodes a polypeptide. This region may encode a precursor form of a mature polypeptide or just the polypeptide.

"PCR" refers to the techniques of the polymerase chain reaction as described in Saiki, et al., *Nature* 324:163 (1986); and Scharf et al., *Science* 233:1076–1078 (1986); U.S. Pat. No. 4,683,195; and U.S. Pat. No. 4,683,202. As used herein, x is "heterologous" with respect to y if x is not naturally associated with y or x is not associated with y in the same manner as is found in nature.

"Homology" refers to the degree of sequence identity between x and y. Typically, the sequence identity between x and y will he at least 50%, usually, the sequence identity will be no less than 60%; more typically, the sequence identity will be no less than 75%; preferably no less than 80%; and even more preferably at least 90%. Most preferably, the sequence identity between x and y will be at least 95%, even more preferably at least 98%, even more preferably at least 99%.

As used herein, the term "polypeptide" refers to a polymer of amino acids and does not refer to a specific length of the product. Thus, peptides, oligopeptides, and proteins are included within the definition of polypeptide. This term also does not exclude post-expression modifications of the polypeptide, for example, glycosylations, acetylations, phosphorylations and the like. Included within the definition are, for example, polypeptides containing one or more analogs of an amino acid (including, for example, unnatural amino acids), polypeptides with substituted linkages, as well as other modifications known in the art, both naturally occurring and non-naturally occurring.

As used herein, "terminators" are regulatory sequences, such as polyadenylation and transcription termination sequences, located 3' or downstream of the stop codon of the coding sequences.

"Recombinant host cells," "host cells," "cells," "cell cultures," and other such terms denote, for example, microorganisms, insect cells, and mammalian cells, that can be or have been used as recipients for introduction of recombinant vector or other transfer DNA, and include the progeny of the cell that has been transformed. Such progeny includes those that may not necessarily be identical in morphology or in genomic or total DNA complement as the original parent that may be produced as a result of natural, accidental, or deliberate mutation. Examples of mammalian host cells include Chinese hamster ovary ("CHO") and monkey kidney ("COS") cells.

As used herein, the term "microorganism" includes prokaryotic and eukaryotic microbial species such as bacteria and fungi, the latter including yeast and filamentous fungi.

"Transformation," as used herein, refers to the transfer of an exogenous polynucleotide into a host cell, irrespective of the method used. for the transfer, which can be, for example, by infection, direct uptake, transduction, F-mating, microinjection or electroporation. The exogenous polynucleotide may be maintained as a non-integrated vector, for example, a plasmid, or alternatively, may be integrated into the host genome.

"Purified" and "isolated" in reference to a polypeptide or a nucleotide sequence means that the indicated molecule is present in substantial absence of other biological macromolecules of the same species or type. The term "purified" as used herein means at least 75% by weight; preferably, at least 85% by weight, more preferably, at least 95% by weight and, most preferably, at least 98% by weight, of biological macromolecules of the same type are present, but water, buffers, and other small molecules, especially molecules having a molecular weight of less than 1000, can be present as well.

By "pharmaceutically acceptable carrier," is meant any carrier that is used by persons in the art for administration into a human that does not itself induce any undesirable side effects such as the production of antibodies, fever, etc. Suitable carriers are typically large, slowly metabolized macromolecules that can be a protein, a polysaccharide, a polylactic acid, a polyglycolic acid, a polymeric amino acid, amino acid copolymers or an inactive virus particle. Such carriers are well known to those of ordinary skill in the art. Preferably the carrier is thyroglobulin.

A "therapeutic composition" herein contains one or more pharmaceutically acceptable carriers, and one or more additional component such as water, saline, glycerol, or ethanol. Additionally, auxiliary substances, such as wetting or emulsifying agents, pH buffering substances, and the like, may be present in such compositions.

By "a therapeutically effective amount," as used herein refers to that amount that is effective for production of a desired result. This amount varies depending upon the health and physical condition of the individual to be treated, the capacity of the individual's immune system to synthesize antibodies, the degree of protection desired, the formulation, the attending physician's assessment of the medical situation, and other relevant factors. It is expected that the amount will fall in a relatively broad range that can be determined through routine trials.

Accordingly, a preferred embodiment of the present invention is a novel unglycosylated KGF fragment, $KGF_{des1-23}$, unaccompanied by impurities which normally accompany the native molecule when it is produced in vivo. This fragment has an apparent molecular weight of about 18 kilo-Daltons ("kD") based upon its migration in Sodium Dodecyl Sulfate Polyacrylamide Gel Electrophoresis ("SDS/PAGE") as a single band (results not shown). The specific activity of purified $KGF_{des1-23}$ on Balb/Mk cells is measured by its $ED_{50}$ value, as defined by the concentration that causes half maximal stimulation of cell proliferation. The $ED_{50}$ of the KGF fragment herein is found to average about 40 pg/ml. The bioactivity of the KGF fragment herein will be at least about 2-fold, preferably, about 7-fold and, more preferably, about 7–10 fold greater than that of the full-length rKGF protein or that of aFGF, when compared in a cell proliferation assay, and 100-fold greater than when $rKGF_{163}$ is bioassayed, using initiation of DNA synthesis in Balb/Mk cells maintained in a chemically defined medium, as described in PCT Patent Application, No. WO 90/08771.

In a preferred embodiment of the present invention, $KGF_{des-1-23}$ is produced by recombinant DNA technology, particularly in the case of large-scale commercial production. A recombinant DNA molecule and an expression vector comprising $KGF_{des1-23}$ in accordance with the present invention can be made and expressed by conventional gene expression technology using methods well-known in the art, as discussed in more detail below.

The present invention also includes analogs of the rKGF fragment that retain the epithelial cell specificity and the at least 2-fold increase in mitogenic activity of $rKGF_{des1-23}$, as compared to the activity of $rKGF_{163}$. In a preferred embodiment, the analog retains the 7-fold, more preferably, the 7–10 fold and, most preferably, the 10-fold increase in mitogenic activity of $rKGF_{des1-23}$. Analogs of $rKGF_{des1-23}$ include post-translationally. modified versions of $rKGF_{des1-23}$, for example, those generated by glycosylations, acetylations, or phosphorylations thereof. Analogs of $rKGF_{des1-23}$ can be also made by conventional techniques of amino acid substitution, deletion, or addition, for example, by site-directed mutagenesis. Thus, all references to embodiments of the present invention as it relates to $rKGF_{des1-23}$ apply equally to analogs thereof.

In one embodiment of the present invention, the KGF fragment can be made by isolating native, mature KGF from cells producing the same and deleting the first 23 N-terminal amino acid residues therefrom. Such deletion can be performed by any conventional techniques known in the art.

In an alternative embodiment, the KGF fragment can be made by isolating the coding sequence of native $KGF_{163}$, deleting the codons that encode the first 23 N-terminal amino acid residues, inserting the modified coding sequence into an expression vector, and transforming host cells with the expression vector to produce the recombinant $KGF_{des1-23}$.

In a further embodiment of the present invention, the KGF fragment can be made by isolating the coding sequence of $KGF_{163}$ from cells known to produce KGF, inserting the coding sequence of $KGF_{163}$ into a baculovirus expression vector, transforming a host insect cell with the baculovirus expression vector, and harvesting and isolating the approximately 18 kD molecular species from the transformed insect cell culture that possesses increased KGF activity, using conventional separatory techniques.

In another embodiment of the present invention, an expression vector containing the $KGF_{des1-23}$ coding sequence can be produced by operably linking the $KGF_{des1-23}$ to one or more regulatory sequences such that the resulting vector is operable in a desired host.

In a further embodiment of the present invention, the coding sequence of $KGF_{des1-23}$ can be obtained by conventional techniques, including the isolation of the coding sequence of $KGF_{163}$ from a cDNA library known to contain such, and deleting therefrom the sequence encoding the first 23 N-terminal amino acid residues. Deletion of the coding sequence of the N-terminal amino acids can be accomplished in vivo or in vitro. The former can be achieved, for example, by expression of the $KGF_{163}$ coding sequence in a baculovirus/insect cell expression system. The latter can be achieved by known PCR techniques using primers that exclude the N-terminal sequences.

In a further embodiment of the present invention, the DNA or vector comprising tne coding sequence of $KGF_{des1-23}$ can be expressed in a prokaryotic or eukaryotic expression system, in particular, a bacterial, mammalian, yeast, or insect cell expression system. In a preferred embodiment, a bacterial or yeast cell expression system may be ideal for production of the $KGF_{des1-23}$ fragment. The yeast cell can be, for example, *Saccharomyces cerevisiae*.

In another embodiment of the present invention, the KGF fragment can be expressed as a fusion protein by linking, in the correct frame and orientation, the 5' end of the $KGF_{des1-23}$ coding sequence to the coding sequence of another molecule that facilitates either intracellular or extracellular production of the $rKGF_{des1-23}$. The coding sequence of such other molecules can be, for example, at least a portion of the prepro α-factor leader sequence, for extracellular expression; the superoxide dismutase ("SOD") gene sequence, or the ubiquitin gene sequence, for intracellular expression in yeast cells.

In yet another embodiment of the present invention, the $rKGF_{des1-23}$ polypeptide can be conjugated to other molecules suitable for its intended use. For example, the $KGF_{des1-23}$ polypeptide can be conjugated to a toxin molecule, such as ricin A, diphtheria toxin, or saporin for destruction of its target cell, i.e., epithelial cells, particularly, keratinocytes.

In a further embodiment, the $KGF_{des1-23}$ polypeptide or a conjugate thereof can be mixed with a pharmaceutically acceptable carrier to produce a therapeutic composition that can be administered for therapeutic purposes, for example, for wound healing, and for treatment of hyperproliferative diseases of the skin and tumors, such as psoriasis and basal cell carcinoma.

The KGF fragment of the present invention can be used for identification of receptor recognition sites as well as for the design of peptide agonists or antagonists. Moreover, in view of the unique specificity of KGF for keratinocytes, its inability to induce the proliferation of vascular endothelial cells or fibroblasts, and its lack of cytotoxicity, $KGF_{des1-23}$ should be a preferred agent of choice for wound healing applications, particularly where there is a desire to promote rev pithelialization of the skin. $KGF_{des1-23}$ should also be particularly useful in corneal epithelial repair. Other applications of $KGF_{des1-23}$ utilize its specificity for epithelial cells found in the gastrointestinal tract.

The choice to select the KGF fragment herein over other growth factors such as epidermal growth factor ("EGF"), platelet-derived growth factor ("PDGF"), and other FGFs for skin repair is within the skill of a person in the art. These other growth factors, for example, induce fibroplasia and angiogenesis, in addition to stimulating, either directly or indirectly, keratinocyte proliferation. In skin repair, such additional activities could produce undesirable side effects such as scarring. In corneal repair involving either a wound or surgery, the use of these factors could induce blood vessel invasion into the cornea, and result in corneal opacity or edema. KGF, on the other hand, has a unique specificity for keratinocytes and does not induce the proliferation of vascular endothetial cells or fibroblasts and, therefore, would be the agent of choice for these particular wound healing applications.

The practice of the present invention will employ, unless otherwise indicated, conventional techniques of molecular biology, microbiology, recombinant DNA, and immunology, which are within the skill of the art. Such techniques are explained fully in the literature, including Sambrook, et al., MOLECULAR CLONING: A LABORATORY MANUAL 2nd ed. (Cold Spring Harbor Laboratory Press, 1989); DNA CLONING, Vol. I and II, D. N Glover ed. (IRL Press, 1985); OLIGONUCLEOTIDE SYNTESIS, M. J. Gait ed. (IRL Press, 1984); NUCLEIC ACID HYBRIDIZATION, B. D. Hames & S. J. Higgins eds. (IRL Press, 1984); TRANSCRIPTION AND TRANSLATION, B. D. Hames & S. J. Higgins eds., (IRL Press, 1984); ANIMAL CELL CULTURE, R. I. Freshney ed. (IRL Press, 1986); IMMOBILIZED CELLS AND ENZYMES, K. Mosbach (IRL Press, 1986); B. Perbal, A PRACTICAL GUIDE TO MOLECULAR CLONING, Wiley (1984); the series, MEFHODS IN ENZYMOLOGY, Academic Press, Inc.; GENE TRANSFER VECTORS FOR MAMA CELLS, J. H. Miller and M. P. Calos eds. (Cold Spring Harbor Laboratory, 1987); METHODS IN ENZYMOLOGY, Vol. 154 and 155, Wu and Grossman, eds., and Wu, ed., respectively (Academic Press, 1987), IMMUNOCHEBICAL METODS IN CELL AND MOLECULAR BIOLOGY, R. J. Mayer and J. H. Walker, eds. (Academic Press London, Harcourt Brace U.S., 1987), PROTEIN PURIFICATION: PRINCIPLES AND PRACTICE, 2nd ed. (Springer-Verlag, N.Y. (1987), and HANDBOOK OF EXPERIMENTAL IMMUNOLOGY, Vol. I–IV, D. M. Weir et al., (Blackwell Scientific Publications, 1986); Kitts et al., *Biotechniques* 14:810–817 (1993); Munemitsu et al., *Mol. and Cell. Biol* 10:5977–5982 (1990).

Standard abbreviations for nucleotides and amino acids are used in FIG. 1 and elsewhere in this specification. All publications, patents, and patent applications cited herein are incorporated by reference.

It has been unexpectedly found that when KGF vector is expressed in insect cells, *Spodoptera fiugiperda* ("SF9") by infection of a recombinant baculovirus, *Autographa californica*, containg the cDNA coding for the mature form of KGF (163 amino acids), they were capable of producing a KGF fragment, a truncated form of KGF that lacks the first 23 amino acid residues of the native KGF N-terminal domain that contains a single glycosylation site. This truncated and unglycosylated KGF fragment designated herein as $KGF_{des1-23}$ or $KGF_{140}$, in contrast to the native long form identified as $KGF_{163}$, has a 7- to 10-fold increased potency on target cells. The target cell specificity of $KGF_{des1-23}$ is unchanged. Additionally, at high concentrations of the KGF fragment, no toxic effect on keratinocytes is observed in contrast to that observed for $KGF_{163}$. These observations suggest that, contrary to what was previously proposed in PCT Application, Publication No. WO 90/08771, the target cell specificity of KGF does not reside in its N-terminal domain. Furthermore, the present invention shows that an N-terminally truncated version of KGP in fact represents an improved KGF version with higher biological activity and decreased cytotoxicity for therapeutic application.

Further, $KGF_{des1-23}$ exhibits a pI more basic than that for $KGF_{163}$. In one assay, the pI was approximately 9.9 for $KGF_{des1-23}$ and 9.4 for $KGF_{163}$. $KGF_{des1-23}$ also exhibits a higher affinity for heparin and for the Mono S resin.

Recombinant $KGF_{des1-23}$, in accordance with the present invention, can be made by well-known recombinant techniques. In this regard, the $KGF_{des1-23}$ coding sequence is operably linked to one or more regulatory sequences in the suitable vector in a proper reading frame and orientation. The vector is suitable when it can replicate or can be replicated to express the recombinant protein in a particular host. Thus, the coding sequence of $KGF_{des1-23}$ can be inserted, for example, into a yeast expression vector for expression in yeast cells, a bacterial expression vector for expression in bacterial cells, a mammalian vector for expression in mammalian cells.

In a preferred embodiment, the coding sequence of $KGF_{des1-23}$ for expression purposes herein is a complementary DNA ("cDNA") molecule encoding $KGF_{des1-23}$. The $KGF_{des1-23}$ cDNA can be made by known recombinant techniques, such as isolating total cellular RNA from a host cell known to express KGF, isolating poly $A^+$ RNA by running the total cellular RNA through an oligo-dT column and eluting the poly $A^+$ RNA therefrom, constructing a cDNA library, using reverse transcriptase, based on the poly $A^+$ RNA isolated, which contains mRNA, and selecting the cDNA clones that contain the $KGF_{des1-23}$ coding sequence by use of labeled oligonucleotide probes constructed on the basis of the known amino acid sequence of $KGF_{des1-23}$.

A regulatory sequence that can be linked to the $KGF_{des1-23}$ coding sequence in the expression vector herein is a promoter that is operable in the host cell in which the recombinant $KGF_{des1-23}$ is to be expressed. Optionally, other regulatory sequences can be used herein, such as one or more of an enhancer sequence, an intron with functional splice donor and acceptance sites, a signal sequence for directing secretion of the recombinant $KGF_{des1-23}$, a polyadenylation sequence, other transcription terminator sequences, and a sequence homologous to the host cell genome. Other sequences, such as an origin of replication, can be added to the vector as well to optimize expression of the desired product. Further, a selectable marker can be present in the expression vector for selection of the presence thereof in the transformed host cells.

The regulatory sequences can be derived from various sources. For example, one or more of them can be associated with a native KGF coding sequence, or derived from or homologous with the host cell in which the sequence is to be expressed, or derived from a microbial, for example, bacterial or yeast source, or hybrids thereof. For use herein, the $KGF_{des1-23}$ coding sequence is, preferably, operably linked downstream of the promoter sequence and upstream of the terminator sequence.

The various components of the expression vector can be linked together directly or, preferably, via Linkers that constitute sites of recognition by restriction enzymes. In one embodiment of the present invention, a promoter sequence herein is linked directly with the $KGF_{des1-23}$ coding sequence, in which case the first amino acid at the N-terminal of the recombinant $KGF_{des1-23}$ protein would be methionine, which is encoded by the ATG start codon. The methionine residue at the N-terminal can be optionally cleaved from the recombinant protein by conventional techniques, for example, in vitro incubation with cyanogen bromide provided no other methionine residues are present in the fragment.

Any promoter that would allow expression of the KGF fragment in a desired host can be used in the present invention. Yeast promoter sequences that are associated with polynucleotide sequences encoding enzymes in the fermentative metabolic pathway are particularly useful in the present invention. Examples of these enzymes include alcohol dehydrogenase ("ADH"), as described in European Patent Application, Publication No. 284 044, enolase, glucokinase, glucose-6-phosphate isomerase, glyceraldehyde-3-phosphate-dehydrogenase ("GAP" or "GAPDH"), hexokinase, phosphofructokinase, 3-phosphoglycerate mutase, and pyruvate kinase ("PyK"), as described in European Patent Application, Publication No. 329 203. In addition, the yeast PHO5 gene, encoding acid phosphatase, as described in Myanohara et al., *Proc. Natl. Acad. Sci. USA* 80:1 (1983), is also useful as a promoter sequence herein.

Other yeast promoters that are suitable herein include, for example, those described in Cohen et al., *Proc. Natl. Acad. Sci. USA* 77:1078 (1980); Henikoff et al., *Nature* 283: 835 (1981); Hollenberg et al., *Curr. Topics Microbiol. Immunol.* 96:119 (1981); Hollenberg et al., "The Expression of Bacterial Antibiotic Resistance Genes in the Yeast *Saccharomyces cerevisiae*," in PLASMIDS OF MEDICAL, ENVIRONMENTAL AND COMMERCIAL IMPORTANCE, K. N. Timmis and A. Puhler, eds. (Amsterdam/New York 1979); Mercerau-Puigalon et al., *Gene* 11:163 (1980); Panthier et al., *Curr. Genet.* 2:109 (1980).

Prokaryotic promoter sequences, optionally containing operator portions, that can be used herein include β-lactamase (penicillinase) and lactose promoter systems, as described in Chang et al., *Nature* 198:1056 (1977), tryptophan promoter system, as described in Goeddel et al., *Nucleic Acids Res.* 8:4057 (1980), and the λ (lambda)-derived $P_L$ promoter.

Preferred mammalian promoter sequences that can be used herein are those from mammalian viruses that are highly expressed and that have a broad host range. Examples include the SV40 early promoter, the Cytomegalovirus ("CMV") immediate early promoter mouse mammary tumor virus long terminal repeat ("LTR") promoter, adenovims major late promoter (Ad MLP), and Herpes Simplex Virus ("HSV") promoter. In addition, promoter sequences derived from non-viral genes, such as the murine metallothionein gene, are also useful herein. These promoters can further be either constitutive or regulated, such as those that can be induced with glucocorticoids in hormone-responsive cells.

Promoters that can be used for insect cell expression in the present invention include the baculovirus polyhedron hybrid promoter and the p10 promoter.

Further, promoters for use in the present invention can be synthetic hybrid promoters that do not occur in nature ("non-natural promoters"), but contain a regulatory region linked with a heterologous expression initiation region. For example, the UAS sequence of one yeast promoter may be joined with the transcription activation region of another yeast promoter, creating a synthetic hybrid promoter. Examples of such promoters include the ADH regulatory sequence linked to the GAP transcription activation region, as described in U.S. Pat. Nos. 4,876,197 and 4,880,734. Other examples include those containing regulatory sequences that are associated with the coding sequences encoding ADH2, GAL4, GAL10, or PHO5, combined with the transcriptional activation region of a glycolytic enzyme, such as GAP or PyK, as described in U.S. Pat. Nos: 4,876,197 and 4,880,734.

Bacterial hybrid promoters include, for example, the tac promoter, as described in De Boer et al. (1983), that is derived from sequences of the trp and lac UV5 promoters. A functional non-natural promoter for use heren may also be a synthetic promoter that is based on a consensus sequence of different promoters.

In another embodiment of the present invention, an enhancer element can be combined with a promoter sequence. Such enhancers not only amplify but also can regulate expression of the $rKGF_{des1-23}$ polypeptide. Suitable enhancer elements for use in mammalian expression systems are, for example, those derived from viruses that have a broad host range, such as the SV40 early gene enhancer, as described in Dijkema et al., *EMBO J.* 4:761 (1985), the enhancer/promoters derived from the LTR of the Rous Sarcoma Virus, as described in Gornan et al., *Proc. Natl. Acad. Sci.* 79:6777 (1982), and from human cytomegalovirus, as described in Boshart et al., *Cell* 41:521 (1985). Additionally, other suitable enhancers include those that can be incorporated into promoter sequences that will become active only in the presence of an inducer, such as a hormone, a metal ion, or an enzyme substrate, as described in Sassone-Corsi and Borelli, *Trends Genet.* 2:215 (1986); and Maniatis et al., *Science* 236:1237 (1987).

For expression in yeast cells, a yeast promoter is preferably used that contains an upstream activator sequence ("UAS") that permits regulated expression of the recombinant $KGF_{des1-23}$. Regulated expression herein may be either positive or negative, thereby either enhancing or reducing transcription. In an alternative embodiment, a UAS can be absent, in which instance, constitutive expression of $KGF_{des1-23}$ would occur.

In another embodiment of the present invention, a transcription termination sequence is placed 3' to the translation stop codon of the $KGF_{des1-23}$ coding sequence. Thus, the terminator sequence, together with the promoter, flank the $KGF_{des1-23}$ coding sequence. Examples of transcription terminator sequences are the yeast-recognized sequences associated with the yeast glycolytic enzymes and those derived from SV40.

In one embodiment of the present invention, the recombinant $KGF_{des1-23}$ can be made to be secreted from the host cell into the growth media by creating chimeric DNA molecules that encode a fusion protein comprised of a leader sequence that contains a secretory signal sequence for secretion of $KGF_{des1-23}$. For the purpose of the present invention, the signal sequences that are suitable for use herein are, for example, those derived from genes for secreted endogenous host cell proteins, such as for the yeast expression system, the yeast invertase gene, as described in European Patent No. 012 873 and Japanese Patent Application, Publication No. 62,096,086, the α-factor gene, as described in U.S. Pat. No. 4,588,684, the prepro α-factor gene, as described in U.S. Pat. No. 4,870,008, and the interferon gene, as described in European Patent No. 060 057.

In a preferred embodiment of the present invention, a truncated yeast α-factor leader sequence can be used. The truncated α-factor leader sequence contains at least a portion of the signal "pre" sequence, and a portion of the "pro" sequence that contains a glycosylation site. Typically, the α-factor leader sequences that can be employed herein include about 25 to about 50 amino acid residues of the N-terminal thereof, as described in U.S. Pat. Nos. 4,546,083 and 4,870,008, and in copending U.S. patent application Ser. No. 07/864,206 and European Patent Application, Publication No. 324 274. Also suitable for use herein are hybrid α-factor leaders made with a "pre" sequence of a first yeast signal sequence, and a "pro" region from a second yeast α-factor as described in PCT Application, Publication No.

WO 89/02463. In one embodiment of the present invention, the signal sequence contains a processing site 5' of the coding sequence of $KGF_{des1-23}$, to allow cleavage thereof, either in vivo or in vitro. For mammalian expression, an example of a suitable leader sequence is the adenovirus tripartite leader that provides for secretion of an operably linked $KGF_{des1-23}$ protein in mammalian cells.

Prokaryotic leader sequences for directing the secretion of recombinant $KGF_{des1-23}$ that are suitable for use herein are those known in the art. For example, such leader sequences include those disclosed in U.S. Pat. No. 4,336,336, relating to "Fused Gene and Method of Making and Using the Same," to T. J. Sithavy et al., issued on Jun. 22, 1982, and U.S. Pat. No. 5,010,015, relating to "Recombinant DNA Molecules and Method for Protein Production," to Palva, I., issued on Apr. 23, 1991.

In another embodiment of the present invention, the expression vector can contain an origin of replication such that it can be maintained as a replicon, capable of autonomous replication and stable maintenance in a host. Such an origin of replication includes those that enable an expression vector to be reproduced at a high copy number in the presence of the appropriate proteins within the cell, for example, the 2 μ and autonomously replicating sequences that are effective in yeast, and the origin of replication of the SV40 viral T-antigen, that is effective in COS-7 cells.

Mammalian replication systems that are suitable for the present invention include those derived from animal viruses that require trans-acting factors to replicate. For example, the replication system of papovaviruses, such as SV40, as described in Gluzman, *Cell* 23:175 (1981), or polyomavirus that replicate to extremely high copy number in the presence of the appropriate viral T antigen. Additional examples include those derived from bovine papillomavirus and Epstein-Barr virus.

Additionally, the expression vector herein can have more than one replication system, thus, allowing it to be maintained, for example, in mammalian cells for expression and in a procaryotic host for cloning and amplification. Examples of such mammalian-bacteria shuttle vectors include pMT2, as described in Kaufman et al., *Mol. Cell. Biol.* 9:946 (1989) and pHEBO, as described in Shimizu et al., *Mol. Cell. Biol.* 6:1074 (1986). Examples of yeast-bacteria shuttle vectors include YEp24, as described in Botstein et al., *Gene* 8:17–24 (1979); pCl/1, as described in Brake et al., *Proc. Natl. Acad. Sci USA* 81: 4642–4646 (1984); and YRpl7, as described in Stinchcomb et al., *J. Mol. Biol.* 158:157 (1982).

The replicon herein may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector can be used herein, depending upon the effect of the vector and the recombinant $KGF_{des1-23}$ on the host. See e.g., Brake et al. (loc. cit.).

In another embodiment of the present invention, the expression vector can be made to integrate into the host cell genome as an integrating vector. The integrating vector herein contains at least one polynucleotide sequence that is homologous to the host cell genome that allows the vector to integrate. Preferably, the host cell contains two homologous sequences flanking the $KGF_{des1-23}$ coding sequence, as described in, for example, European Patent Application, Publication No. 127 328, relating to integrating vectors constructed with DNA from various Bacillus strains integrated into the Bacillus chromosome. Integrating vectors may also be comprised of bacteriophage or transposon sequences.

The homologous sequences, however, need not be linked to the expression vector. For example, an expression vector can be used that can integrate into the CHO genome via an unattached dihydrofolate reductase gene. In a preferred embodiment, the homologous sequences flank the $KGF_{des1-23}$ coding sequence in the vector. Particularly useful homologous yeast genome sequences for the present invention are, for example, those disclosed in PCT Application, Publication No. WO 90/01800, and the his4 gene sequences, as described in Genbank, accession no. J01331.

In another embodiment of the present invention, one or more selectable markers can be attached to other components in the expression vector to allow for the selection of the host cells that have been transformed. Selectable markers that can be expressed in a host cell include genes that can render the host cell resistant to drugs such as tunicamycin, G418, ampicillin, chloramphenicol, erythromycin, kanamycin (neomycin), and tetracycline, as described in Davies et al., *Ann. Rev. Microbiol.* 32:469 (1978). Selectable markers herein also include biosynthetic genes, such as those in the histidine, tryptophan, and leucine biosynthetic pathways, such as ade2, his4, leu2, trp1. Thus, for example, when a leu⁻ host cell is used as recipient in transformation with an expression vector, and leucine is absent from the media, for example, only the cells that carry a plasmid with a leu⁺ gene will survive.

In addition, selectable markers that provide the host cells with the ability to grow in the presence of toxic compounds, such as metal, is also suitable herein; for instance, the presence of cup1 allows yeasts to grow in the presence of copper ions, as described in Butt et al., *Microbiol. Rev.* 51:351 (1987).

The method for construction of an expression vector for transformation of insect cells for expression of recombinant $KGF_{des1-23}$ herein is slightly different than that generally applicable to the construction of a bacterial expression vector, a yeast expression vector, or a mammalian expression vector. In an embodiment of the present invention, a baculovirus vector is constructed in accordance with techniques that are known in the art, for example, as described in Kitts et al., *BioTechniques* 14:810–817 (1993), Smith et al., *Mol. Cell. Biol.* 3:2156 (1983), and Luckow and Summer, *Virol.* 17:31 (1989). In one embodiment of the present invention, a baculovirus expression vector is constructed substantially in accordance to Summers and Smith, Texas Agricultural Experiment Station Bulletin No. 1555 (1987). Moreover, materials and methods for baculovirus/insect cell expression systems are commercially available in kit form, for example, the MaxBac® kit from Invitrogen (San Diego, Calif.).

Briefly, a KGF expression cassette including the $KGF_{des1-23}$ coding sequence and optionally, a regulatory sequence, a selectable marker, etc., can be first constructed by insertion of the $KGF_{163}$ or $KGF_{des1-23}$ coding sequence into a baculovirus transfer vector that contains at least an essential polynucleotide sequence, as described in more detail below, and/or a polynucleotide sequence that is homologous to a portion of the. baculovirus genome ("the baculovirus sequences") and is capable of homologous recombination therewith, for example, the polyhedron gene. Insertion therein can be engineered at a restriction enzyme site, as described in Miller et al., *Bioassays* 4:91 (1989). In a preferred embodiment, a KGFd$_{1-23}$ coding sequence is positioned downstream from the polyhedron promoter and flanked at both the 5' and the 3' end by polyhedron-specific sequences.

The KGF$_{163}$ coding sequence can be obtained by known recombinant techniques from cells that are known to express KGF activity. The transfer vector containing the KGF$_{des1-23}$ coding sequence is co-transfected into host insect cells together with a mutant of wild-type baculovirus, so as to form a recombinant baculovirus. This mutant baculovirus lacks an essential polynucleotide sequence necessary for production of a functional recombinant virus. In this regard, a functional virus is one that is capable of independent replication in a host. A functional recombinant virus is obtained when the mutant baculovirus and the transfer vector carrying the KGF expression cassette both infect a host insect cell and recombine therein.

Recombinant baculoviruses can be identified by known methods. For example, the wild-type viruses produce a polyhedron protein at very high levels in the nuclei of infected cells during a late stage of viral infection. Accumulated polyhedron protein forms occlusion bodies that also contain embedded viral particles. These occlusion bodies, up to 15 µm in size, are highly refractile, giving them a bright shiny appearance that is readily visualized under the light microscope. Cells infected with recombinant viruses lack occlusion bodies. Recombinant virus and wild-type virus can, therefore, be distinguished by plating the transfection supernatant or dilutions thereof onto a monolayer of insect cells by standard techniques. The plaques can then be screened under the light microscope for the presence, indicative of wild-type virus, or absence, indicative of recombinant virus, of occlusion bodies, as described in Vol 2. of CURRENT PROTOCOLS IN MOLECULAR MICROBIOLOGY 16.8 F. M. Ausubel et al. eds, Supp. 10, Green Publisher Associates and Wiley Interscience (1990).

The functional recombinant baculovirus containing the KGF expression cassette obtained in this manner is suitable for transfection into new host insect cells for production of large quantities of the recombinant KGF$_{des1-23}$. Recombinant KGF$_{des1-23}$ produced in this manner can be separated from KGF$_{163}$ based upon molecular weight differences, using known separatory techniques.

When making rather than purchasing a commercially available baculovirus/insect cell expression kit, the baculovirus transfer vector herein can be made by linking different components together, such as a promoter, a secretory leader sequence, and a transcription termination sequence. Alternatively, the transfer vector can be constructed such that a single copy of the KGF$_{des1-23}$ coding sequence is operably linked to one or more regulatory elements, or multiple copies of the KGF$_{des1-23}$ coding sequence are each operably linked to its own set of regulatory elements. As a further alternative. multiple. copies of the KGF$_{des1-23}$ coding sequence can be regulated by the same set of regulatory elements.

The transfer vector for the present invention may optionally contain an origin of replication so that it can be maintained as a replicon that is capable of stable maintenance in a host, such as a bacterium, for cloning and amplification. In a preferred embodiment of the present invention, the transfer vector for introducing KGF$_{des1-23}$ into AcNPV is pAc373. Other vectors, known to those of skill in the art, can also be used, including, for example, pVL985, which alters the polyhedrin start codon from ATG to ATT, and which introduces a BamHI cloning site 32 basepairs downstream from the ATT, as described in Luckow and Summers, *Virol.* 17:31 (1989). After the expression vector is made, the vector is used to transform host cells for expression of recombinant KGF$_{des1-23}$. The host cells that are suitable for use herein includes prokaryotes and eukaryotes. The prokaryotes include Gram positive and Gram negative bacteria. The eukaryotes include fungi, yeast, mammalian, and insect cells. The bacterial hosts include, for example, Campylobacter, Bacillus, Escherichia, Lactobacillus, Pseudomonas, Staphylococcus, and Streptococcus. Yeast hosts from the following genera may be utilized: Candida, Hansenula, Kluyveromyces, Pichia, Saccharomyces, Schizosaccharomyces, and Yarrowia. Mammalian cell lines suitable for use herein include, for example, many immortalized cell lines available from the American Type Culture Collection (ATCC), such as Chinese hamster ovary ("CHO") cells, HeLa cells, baby hamster kidney ("BHK") cells, monkey kidney cells ("COS"), and human hepatocellular carcinoma cells such as Hep G2. A number of insect cell hosts are also suitable for expression of the KGF fragment or analog, including, for example, *Aedes aegypti, Autographa californica, Bombyx mori, Drosophila melanogaster,* and *Spodoptera frugiperda,* as described in PCT Application, Publication No. WO 89/046699; Carbonell et al., *J. Virol.* 56:153 (1985); Wright *Nature* 321:718 (1986); Smith et al., *Mol. Cell. Biol.* 3:2156 (1983); and generally, Fraser, et al. in vitro *Cell. Dev. Biol.* 25:225 (1989).

Certain expression vectors, either extra-hromosomal replicons or integrating vectors, have been developed for transformation into certain hosts. A person of ordinary skill in the art would be able to adopt or adapt one or more of these developed vectors for use herein. For example, expression vectors have been developed for the following bacterial hosts that can be used herein: *Bacillus subtilis,* as described Palva et al., *Proc. Natl. Acad. Sci. USA* 79:5582 (1982); European Patent No. 036 259 U.S. Pat. No. 4,711,843 and European Patent Application, Publication No. 063 953; PCT Application, Publication No. WO 84/04541, U.S. Pat. No. 4,663,280; *Escherichia coli,* Shimatake et al., *Nature* 292:128 (1981); Amann et al., *Gene* 40:183 (1985); Studier et al., *J. Mol. Biol.* 189:113 (1986); European Patent No. 036 776 and European Patent Application, Publication Nos. 136 829 and 136 907; *Streptococcus cremoris,* Powell et al., *Appl. Environ. Microbiol.* 54:655 (1988); *Streptococcus lividans,* Powell et al., *Appl. Environ. Microbiol.* 54:655 (1988); *Streptomyces lividans,* U.S. Pat. No. 4,745,056.

Expression vectors that have been develop ed for yeasts that can be used herein include, for example, *Candida albicans* as described in Kurtz, et al. *Mol. Cell. Biol.* 6:142 (1986); *Candida maltosa* in Kunze, et al. *J. Basic Microbiol.* 25:141 (1985); *Hansenula polymorpha,* in Gleeson, et al. *J. Gen. Microbiol.* 132:3459 (1986); Roggenkamp et al. *Mol. Gen. Genet.* 202:302 (1986); *Kluyveromyces fragilis,* in Das, et al. *J. Bacteriol.* 158:1165 (1984); *Kluyveromyces lactis,* in De Louvencourt et al. *J. Bacteriol.* 154:737 (1983); Van den Berg et al. *BiolTechnology* 8:135 (1990); *Pichia guillerimondii,* in Kunze et al. *J. Basic Microbiol.* 25:141 (1985); *Pichia pastoris,* in Cregg et al. *Mol. Cell. Biol.* 5:3376 (1985); U.S. Pat. No. 4,837,148 and U.S. Pat. No. 4,929,555; *Saccharomyces cerevisiae,* in Hinnen et al. *Proc. Natl. Acad. Sci. USA* 75:1929 (1978); Ito et al. *J. Bacteriol.* 153:163 (1983); *Schizosaccharomyces pombe,* in Beach and Nurse, *Nature* 300:706 (1981); and *Yarrowia. lipolytica* in Davidow, et al., *Curr. Genet.* 10:380–471 (1985); Gaillardin et al., *Curr. Genet.* 10:49 (1985).

The transformation procedures suitable for use herein are those known in the art and include, for example, first treating the bacterial cells with $CaCl_2$ or other agents, such as divalent cations and DMSO, and incubating the treated cells with the $KGF_{des1-23}$ coding sequence. DNA can also be introduced into bacterial cells by electroporation. The exact transformation procedure varies with the bacterial species to be transformed as described in, for example, Masson et al., *FEMS Microbiol. Lett.* 60:273 (1989); Palva et al., *Proc. Natl. Acad. Sci. USA* 79:5582 (1982); European Patent Application, Pub. Nos. 036 259 and 063 953; PCT Application, Publication No. W084/04541, for Bacillus; Miller et al., *Proc. Natl. Acad. Sci.* 85:856 (1988); Wang et al., *J. Bacteriol.* 172:949 (1990), for Qumpylobacter, Cohen et al., *Proc. Natl. Acad. Sci.* 69:2110 (1973); Dower et al., *Nucleic Acids Res.* 16:6127 (1988); Kushner "An improved method for transformation of *Escherichia coli* with ColEl-derived plasmids", in GENETIC ENGINEERING: PROCEEDINGS OF THE INTERNONAL SYMPOSIUM ON GENETIC ENGINEERING, H. W. Boyer and S. Nicosia, eds, Amsterdam and New York, Elsevier and North Holland Biomedical Press (1978); Mandel et al., *J. Mol. Biol.* 53:159 (1970); Taketo, *Biochim. Biophys. Acta* 949:318 (1988), for Escherichia; Chassy et al., *FEMS Microbiol. Lett.* 44:173 (1987), for Lactobacillus; Fiedler et al., *Anal. Biochem.* 170:38 (1988), for Pseudomonas; Augustin et al., *FRMS Microbiol. Leti.* 66:203 (1990), for Staphylococcus; Barany et al,. *J. Bacteriol.* 144:698 (1980); Harlander "Transformation of *Streptococcus lactis* by Electroporation", in STREPTOCOCCAL GENETICS, J. Petretti and R. Curtiss III, eds (1987); Perry et al., *Infec. Immun.* 32:1295 (1981); Powell et al., *Appl. Environ. Microbiol.* 54:655 (1988); Somkuti et al., *Proc. 4th Evr. Cong. Biotechnology* 1:412 (1987), for Streptococcus.

For yeast, the transformation procedures that can be used herein include electroporation, as described in "Guide to Yeast Genetics and Molecular Biology," Vol 194 METHODS IN ENZYMOLOGY, C. Guthrie and G. R. Fink, (Academic Press 1991). Other procedures include the transformation of spheroplasts or the transformation of alkali cation-treated intact cells. Such procedures are described in, for example, Kurtz et al., *Mol. Cell. Biol.* 6:142 (1986); Kunze et al,. *J. Basic Microbiol.* 25:141 (1985), for Candida; Gleeson et al,. *J. Gen. Microbiol.* 132:3459 (1986); Roggenkamp et al., *Mol. Gen. Genet.* 202:302, for Hansenula (1986); Das et al,. *J. Bacteriol.* 158:1165 (1984); De Louvencourt et al,. *J. Bacteriol.* 154:1165 (1983); Van den Berg et al., BiolTechnology 8:135 (1990) for Kluyveromyces; Cregg et al., *Mol. Cell. Biol.* 5:3376 (1985); Kunze et al,. *J. Basic Microbiol.* 25:141 (1985); U.S. Pat. No. 4,837,148 and U.S. Pat. No. 4,929,555, for Pichia; Hinnen et al., Proc. Natl. Acad. Sci. USA 75;1929 (1978); Ito et al,. *J. Bacteriol.* 153:163 (1983), for Saccharomyces; Beach and Nurse *Nature* 300:706 (1981), for Schizosaccharomyces; Davidow et al., *Curr. Genet.* 10:39 (1985); Gaillardin et al., *Curr. Genet.* 10:49 (1985), for Yarrowia.

For example, for mammalian cell systems, such methods include dextran-mediated transfection, calcium phosphate precipitation, polybrene-mediated transfection, protoplast fusion, electroporation, encapsulation of the $KGF_{des1-23}$ polynucleotide in liposomes, and direct microinjection of the DNA into nuclei.

Immunoassays and activity assays that are known in the art can be utilized herein to determine if the transformed host cells are expressing the desired KGF fragment. For example. for detection of intracellular production of $KGF_{des1-23}$ by transformed host cells, an immunofluorescence assay can be performed on the transformed host cells without separating the KGF fragments from the cell membrane. In this assay, the host cells are first fixed onto a solid support, such as a microscope slide or microtiter well. Next, the fixed host cells are exposed to an anti-KGF antibody. Preferably, to increase the sensitivity of the assay, the fixed cells are exposed to a second antibody, that is labelled and binds to the anti-KGF antibody. For instance, the secondary antibody may be labelled with an fluorescent marker. The host cells which express the KGF fragments will be fluorescently labelled can be visualized under the microscope.

In another embodiment of the present invention, the recombinant $KGF_{des1-23}$ polypeptide can be expressed as a fusion protein in any of the above expression systems. For example, for yeast expression, in the construction of an expression vector, a DNA sequence encoding the N-terminal portion of an endogenous yeast protein, or other stable protein, can be fused to the 5' end of the coding sequence of $KGF_{des1-234}$. The DNA sequence at the junction of the two amino acid sequences optionally encodes a cleavable site, as discussed in European Patent Application, Publication No. 196 056.

An example of a DNA sequence that encodes the N-terminal portion of the fusion protein is the sequence encoding at least a portion of yeast or human superoxide dismutase ("SOD") for expression in yeast. Another example is the sequence encoding at least a portion of the ubiquitin protein, preferably, containing the sequence that encodes the cleavage site or its processing enzyme, the ubiquitin-specific processing protease. See, e.g., PCT Application Publ. No. WO 88/024066.

KGF toxin conjugates suitable for use herein can be produced by methods known in the art, for example, U.S. Pat. Nos. 4,771,128, 4,808,705, and 4,894,443 and PCT Application, Publ. No. WO 92/04918.

The present invention includes variants and modifications of the above that do not substantially alter the nature and activity of the fragment, conjugate, therapeutic composition, vector, host, and methods of use and that are apparent to a person of ordinary skill in the art.

EXAMPLES

The examples presented below are provided to demonstrate the present invention, and are not to be construed as limiting the invention in any way.

Example 1

The Production of a KGF Coding Sequence Linked to a Signal Peptide

PCR techniques were applied to the construction of the $KGF_{163}$ coding sequence linked to a signal peptide, SEQ ID NO: 1. The signal peptide was one that was associated with the native $KGF_{163}$ coding sequence, as described in Finch et al., *Science* 245:752–755 (1989).

The following primers were used to clone the $KGF_{163}$ coding sequence and its signal peptide from a human kidney cDNA library:

```
SEQ ID NO: 4 (sense primer)
          PstI       Met His Lys Trp Ile Leu*
5' AGATCTCTGCAGCTATA ATG CAC AAA TGG ATA CTG 3'

SEQ ID NO: 6 (antisense primer)
          NotI   Stop Thr Ile Ala Met Pro Leu Phe**
5' AGATCTGCGGCCGC TTA  AGT TAT TGC CAT AGG AAG AAA 3'
```

*The peptide sequence is listed in the Sequence Listing as SEQ ID NO: 3.
**As encoded by the reverse complement of the primer, and the peptide sequence is listed as SEQ ID NO: 5.

As shown in the sequences above, in addition to the $KGF_{163}$ coding sequence and the signal peptide, additional nucleotides were incorporated at the 5' and the 3' ends, respectively. The additional nucleotides include a PstI site at the 5' end, and a NotI site at the 3' end of the respective primers, to facilitate cloning of the $KGF_{163}$ coding sequence and its signal peptide into the desired insect cell transfer vector. (See Example 2 below.)

To generate the desired $KGF_{163}$ DNA molecule, 1 μl of each primer, at a final concentration of 1 μM, was added to 2.5 μl or approximately 10 ng, of human kidney cDNA library, obtained from Clontech, Palo Alto, Calif., U.S.A. The following reagents from the Perkin-Elmer PCR kit (Norwalk, Connecticut, U.S.A.) were also added to the primer/cDNA library: 16 μl of 1.25 mM dNTP, containing equimolar amounts of each of DATP, dTPP, dCTP and dGTP, 10 μl of 10×buffer, 0.5 μl of Taq polymerase, at 5 units/ml; and 69 μl of water. PCR was performed on a DNA Thermal Cycler, from Perkin Elmer, Norwalk, Conn., U.S.A., as follows: 94° C. for 1 minute, 55° C. for 2 minutes, and 72° C. for 3 minutes. This temperature cycle was treated 30 times. The resulting PCR product was treated with DNA Poll (Klenow) and then phenol/chloroform extracted, chloroform extracted, and ethanol precipitated, respectively.

The PCR product was digested with PstI and NotI and gel purified before ligation.

Example 2

The Production of a KGF Insect Cell Expression Vector

The purified PCR product, comprising the $KGF_{163}$ coding sequence and its signal peptide, was inserted into a baculovirus transfer vector. The specific baculovirus used is *Autographa californica* nuclearpolyhedrosis virus (AcNPV).

The purified PCR product from Example 1, digested with restriction enzymes PstI and NotI, was ligated to pAcC13, which was also digested with PstI and NotI. pAcC13 is a baculovirus transfer vector and is depicted in FIG. 2. This plasmid was derived from pAcC12, as described in Munemitsu et al., *Mol. Cell. Biol.* 10:5977–5982 (1990) and a derivative of the pVL941 transfer vector, the construction of which is described in Quilliam et al., *Mol. Cell. Biol.* 10:2901–2908 (1990); Luckow et al., *Virol.* 170:31–39 (1989); and Smith et al., *Mol. Cell. Bio.* 3(12): 2156–2165 (1983).

The transfer vector further contains a polylinker conveniently placed between the baculovirus polyhedrin promoter and terminator. The DNA sequence of the polylinker comprises unique restriction sites. Thus, by digesting the transfer vector with the PstI and NotI sites within the polylinker, the $KGF_{163}$ coding sequence and the signal peptide can be inserted between the polyhedrin promoter and terminator. In addition, the transfer vector contains sequences from the essential gene of AcNPV baculovirus. The transfer vector was named pAcc/KGF.

Example 3

The Production of a Recombinant Baculovirus Capable of Expressing the KGF Coding Sequence The transfer vector with the $KGF_{163}$ coding sequence and its signal peptide insert was transfected together with a mutant baculovirus into *Spodoptera frugiperda*, SF9 cells. The mutant baculovirus is a derivative of AcNPV that lacks a functional essential gene. This mutant baculovirus must recombine with the transfer vector to produce a viable baculovirus. To increase the number of recombinants, the mutant baculovirus was linearized with BsuI. In this regard, several BsuI sites were incorporated into the mutant baculovirus for this purpose. This mutant baculovirus is similar to the baculovirus described in Kitts et al., *Biotechniques* 14(5):810–817 (1993).

A. Preparation of Recombinant Baculovirus

First, $1 \times 10^6$ SF9 cells were seeded per well in a 6-well plate containing 2 ml of a complete TNMFH medium. The cells were incubated for at least 30 minutes at room temperature to allow the cells to attach to the plate. The complete TNMFH medium contained GRACE'S medium obtained from JRH Biosciences, Lenexa, Kans., U.S.A. and supplemented with 10% (v/v) fetal bovine serum (56° C. heat inactivated for 30 minutes), 3% (w/v) Yeastolate (Difco, Detroit, Mich., U.S.A.), and 1% (v/v) Fungi-BACT (Irvine Scientific, Santa Ana, Calif., U.S.A.).

For addition to each of the above wells, the following transfection mixture was initially separately prepared by first, adding 0.5 ml of GRACE'S medium containing no supplement into a sterile 1.5 ml eppendorf tube; next, adding 0.5 μg of linearized mutant baculovirus DNA and, approximately, 2–3 μg of the transfer vector containing the $KGF_{163}$ coding sequence and the signal peptide insert. This is approximately a 4:1 ratio of transfer vector to mutant baculovirus. Finally, the cationic liposome solution, BRL catalog #8282SA (from BRL, Gaithersburg, Md., U.S.A.) was mixed thoroughly, and 10 μl of this liposome solution were added to the baculovirus mixture. This transfection mixture was incubated at room temperature for 15 minutes.

Before the transfection mixture was added to the cells in the wells, the TNMFH medium was removed therefrom, and the cells were washed with 1–2 ml of GRACE'S medium without supplements. When the transfection mixture was finally prepared, as described above, all the media were removed from the SF9 cells, and the transfection mixture was added dropwise to the cells. The 6-well plate was then covered with pamfilm to reduce evaporation of the transfection mixture. The plate was rocked slowly at room temperature for approximately four hours on a Bellco®, catalog no. #774020020, Vineland, N.J., U.S.A., side/side rocking platform at setting 2.5.

After the incubation of the cells with the transfection mixture, 0.5 ml of complete TNMFH medium was added to the cells and the mixture was incubated at 27° C. in a humidified chamber (92%) for 48 hours. Thereafter, the medium containing recombinant baculovirus was removed from the cells and stored at 4° C. until the plaque assay for recombinant virus isolation was performed. This medium constituted the primary source of the recombinant virus.

After the medium was removed from the cells, 2 ml of complete TNMFH were added to the cells, and the cells were further incubated in a humidified chamber (92%) at 27° C. for another 48–72 hours. This final step was performed to provide a back-up source of recombinant virus and to provide a visual record of the viral infection.

B. Plaque Purification of the Recombinant Baculovirus

The recombinant KGF baculoviruses prepared as above were plaque-purified according to the following steps:

First, 4 ml of SF9 cells at 5×105 cells/ml in GRACE'S medium were plated on 60 mm LUX dishes, catalog #5220. The cells were incubated at room temperature for 20–30 minutes to allow the cells to adhere to the plate. In the meantime, the medium containing the primary source of recombinant virus was diluted into 2 ml of TNMFH medium at 1:10, 1:50, 1:100, and 1:200 dilutions. After the cells were allowed to adhere, the medium was aspirated from the adherent cells, and the various dilutions of the recombinant virus were added quickly so as not to allow the cells to dry. The cells were then incubated for 1 hour at 27° C. in a humidified chamber (92%).

Ten minutes before the incubation was complete, an agarose solution was prepared. A 2×concentration of GRACE'S medium supplemented as before was heated to 37° C. Only the amount used for the assay was heated; otherwise, proteins may precipitate upon repeated heating. When the 2×medium was warm, a 3% (w/v) Sea Plaque agarose mixture in water was melted in a microwave and immediately mixed 1:1 with the 2×medium. The agarose solution was then allowed to cool at room temperature for several minutes.

The viral medium was aspirated from the cells in the dishes by tilting the dishes slightly on the hood rim. The dishes were then drained for a few seconds and aspirated again to remove as much liquid as possible. This second aspiration step was included to reduce the likelihood of virus spreading and causing indistinct plaques. Six dishes or fewer were handled at a time to avoid drying the cells. The aspirated dishes were never left exposed with the lids off for more than a few seconds.

Next, 4 ml of the agarose solution were added to each dish and left undisturbed for 15 minutes. The agarose overlay was dried by lifting the lids to the side of the plate to permit the agarose to dry for approximately 25 minutes. Then, the dishes were covered with the lids, and the cells were incubated in a humidified chamber (92%) for 4 days at 27° C.

To facilitate visualization of the plaques, the dishes were stained with 2 ml per dish of 25% (w/v) Sea Plaque agarose in complete TNMFH medium with 0.01% (v/v) neutral red, from Sigma, St. Louis, Mo., U.S.A. The agarose overlay was dried at room temperature for about one hour with the lids on, before the dishes were returned to a humidified chamber (92%) at 27° C. for 3–4 hours. The neutral red dye was incorporated by the viable but not the dead cells.

When the plaques were well-resolved, 7 individual plugs were picked with a sterile Pasteur pipet and each was transferred to 1 ml of complete TNMFH. The plugs were incubated for 2 days at room temperature. The plugs were then vortexed, and the plaque assay was repeated with 50 µl of this solution.

C. Expansion of the Plaque Purified Baculovirus

To expand the viral titers, 3–4 plugs of each baculovirus clone from the second round of plaque purification were placed directly onto cultures of SF9 cells. The cells were plated at $2.5 \times 10^5$/well in 6-well plates with 2.5 ml of complete TNMFH medium. The cells and virus were then incubated for approximately 4 hours at 27° C. in a humidified chamber (92%).

For the second round of expansion, all the virus from the 6-well plates were transferred to 10 cm dishes. The 10 cm dishes were plated with $7.5 \times 10^6$ cells in 7.5 ml of complete TNMFH media. The cells and virus were incubated for 48–72 hours at 27° C. in a humidified chamber (92%).

After this infection, the cells were thoroughly screened for any wild type virus contamination that appeared as infected cells containing occlusion bodies. No occlusion bodies were observed. The resulting recombinant baculovirus was named KGF-5. and was deposited with the American Type Culture Collection ("ATCC") at 12301 Parklawn Drive, Rockville, Md., U.S.A. 20852–1776 on Jun. 17, 1993, Accession No. VR2411.

Supernatant from the second baculovirus expansion round was tested for KGF bioactivity. Also, the crude supernatant was run on a sodium dodecyl sulfate polyacrylamide gel electrophoresis ("SDS-PAGE") gel, and stained with Coomassie blue to confirm the expression of KGF.

Example 4

Baculovirus Expression of a KGF Coding Sequence

SF9 insect cells were infected with the recombinant baculovirus, as described in Example 3, to provide a large of amount of recombinant KGF fragments for purification and analysis.

More specifically, SF9 cells were diluted to a cell density of $1 \times 10^6$ cells/ml in Excell-400 (JRH Biosciences, Lenexa, Kans. U.S.A.). The cells were seeded into either a 1 L or 2 L shake flask with 300 ml or 500 ml of medium, respectively. Virus from the second expansion (described in Example 3, section C) was used to inoculate the cells at 10% (v/v) dilution. The cells and virus were shaken at approximately 131 rpm with the caps of the shake flasks loosened to provide an adequate air supply. The cells were incubated at 27° C. for 48 hrs.

Conditioned medium from the incubated cell culture above was collected by centrifuging the cell culture at 15,000×g for 10 minutes at 4° C. to remove the cells. Next, the conditioned medium was filtered with an 0.8 µm cellulose nitrate filter (Milipore). Approximately 5 liters of this conditioned medium was concentrated to 200 ml using a filtron cassette system (Omega membrane), having a 3 kD molecular weight cut-off. The pH of the retentate was adjusted to 7.2 with IN NaOH and the small amount of precipitate was removed by centrifugation at 10,000×g for 20 minutes at 4° C.). The concentrated conditioned medium was then immediately applied to a Heparin Sepharose® ("HS") resin column.

Example 5

Purification of a $KGF_{des1-23}$ Fragment

Recombinant $KGF_{des1-23}$ from the concentrated conditioned medium described in Example 4 was purified by HS affinity chromatography, followed by Mono S cation exchange chromatography. The recombinant $KGF_{des1-23}$ bound to the HS was eluted using step-wise salt gradient. Next, the recombinant $KGF_{des1-23}$ eluted from the HS column was bound to the Mono S cation column and was eluted using a linear salt gradient.

Further details of the procedure utilized are described below.

A. Heparin Sepharose® Affinity Chromatography

First, the concentrated conditioned medium from Example 4 was allowed to run for approximately 2 hours at 4° C. through a 30 ml bed of HS resin. The column was equilibrated in a buffer containing 150 mM NaCl, and 10 mM Tris-HCl at pH 7.3. Once the concentrated conditioned medium was loaded, the column was washed extensively with the equilibration buffer until the absorbance at 280 nm returned to baseline. Then, protein was eluted from the HS column with an increasing step-wise NaCl gradient. The NaCl concentrations were 0.45 M, 1 M, and 2 M NaCl, in 10 mM Tris-HCl at pH 7.3. The flow rate of the column during elution was approximately 90 ml/hr and 3-ml size fractions were collected.

The fractions were tested for KGF bioactivity utilizing Balb/Mk cells. The assay is described in section C below. The fractions with the highest bioactivity were eluted with 1 M NaCl and were pooled. Before the pooled fractions were loaded onto the next column, the fractions were diluted five-fold with 10 mM Tris-HCl at pH 7.2 to a final salt concentration of 0.2 M NaCl.

B. Mono S Cation Exchange Chromatography

The pooled fractions eluted from the HS column were loaded with a Super loop onto a Mono S column linked to an FPLC system (Pharmacia, Piscataway, N.J.). The Mono S cation exchange column was equilibrated with 10 mM Tris-HCl at pH 7.2. When the pooled fractions were loaded, the column was washed extensively at a flow rate of 1 ml/min. with the equilibration buffer until the absorbance returned to baseline. Then, protein was eluted from the column with a linear NaCl gradient, 0.2 M to 1 M NaCl in 10 mM Tris-HCl at pH 7.3 at a flow rate of 1 mil/min., and 1 ml fractions were collected.

Two major protein peaks of activity were found that eluted at about 0.55 M NaCl and 0.60 M NaCl. Fractions across the protein peaks were assayed for bioactivity and subjected to SDS-PAGE analysis. The results of the gel analysis (not illustrated) showed that protein from 0.55 M and 0.60 M NaCl fractions exhibited an apparent molecular weight of 27 kD and 18 kD, respectively.

When the bioactivity of the fractions was determined, the 18 kD protein was found to exhibit at least a 2-, but more particularly a 7–10 fold more activity than the 27 kD protein, or than the positive control, the acidic fibroblast growth factor ("aFGF"), as shown in FIG. 5. The bioactivity of the fractions were tested using Balb/Mk cells. (See section C, below.)

To determine the amino acid sequence of the eluted protein, two 100 pmole samples of the 27 kD and 18 kD proteins were subjected to Edman degradation after centrifugal adsorption to polyvinylidene difluoride (PVDF, Applied Biosystems Prospin). The samples were loaded onto an Applied Biosystems 470A or 473A protein sequencer. Twenty rounds of Edman degradation were carried out using standard software and chemicals supplied by Applied Biosystems, and identifications of PTh-amino acids were made with an automated on-line HPLC system (PTH analyzer 120A, Applied Biosystems).

Using standard methodology well known in the art, an unambiguous amino acid sequence was established for posi-tions 1 to 20 of the N-terminal of the 18 kD protein, which is $KGF_{des1-23}$. The sequence was as follows:

S Y D Y M E G G D I R V R R L F X R T Q (SEQ ID NO: 7). The N-terminal sequence of the 27 kD protein is identical to the N-terminal sequence of $KGF_{163}$.

C. KGF Bioactivity Assay Utilizing Balb/Mk Cells

KGP bioactivity was assessed by the ability of the fractions to promote growth of BALB/C-Mk cells.

Stock cultures of Balb/Mk cells were grown and maintained in low calcium Dulbecco's modified Eagle medium supplemented with 10% fetal bovine serum, 0.25 µg/ml fungizone, and 10 ng/ml aPGF. The cells were incubated at 37° C. in a 10% $CO_2$ atmosphere with 99% humidity. For the bioactivity assay, the cells were seeded in 12-well plates at a density of $5 \times 10^3$ cells per well in 1 ml of medium as described above for the stock cultures, and as described in Gospodarowicz et al,. *J. Cell. Physiol.* 142:325–333 (1990).

Ten microliter aliquots of the desired column fractions were diluted into 1 ml of 0.2% (w/v) gelatin in phosphate buffered saline ("PBS"). Ten microliters of this dilution were added to Balb/Mk cells seeded in 12-well cluster plates containing 22 mm wells, at $5 \times 10^3$ cells per well, and a 10 µl aliquot of either the diluted column fractions or medium containing 10 ng aFGF were added to the cells every other day.

Figure 4:
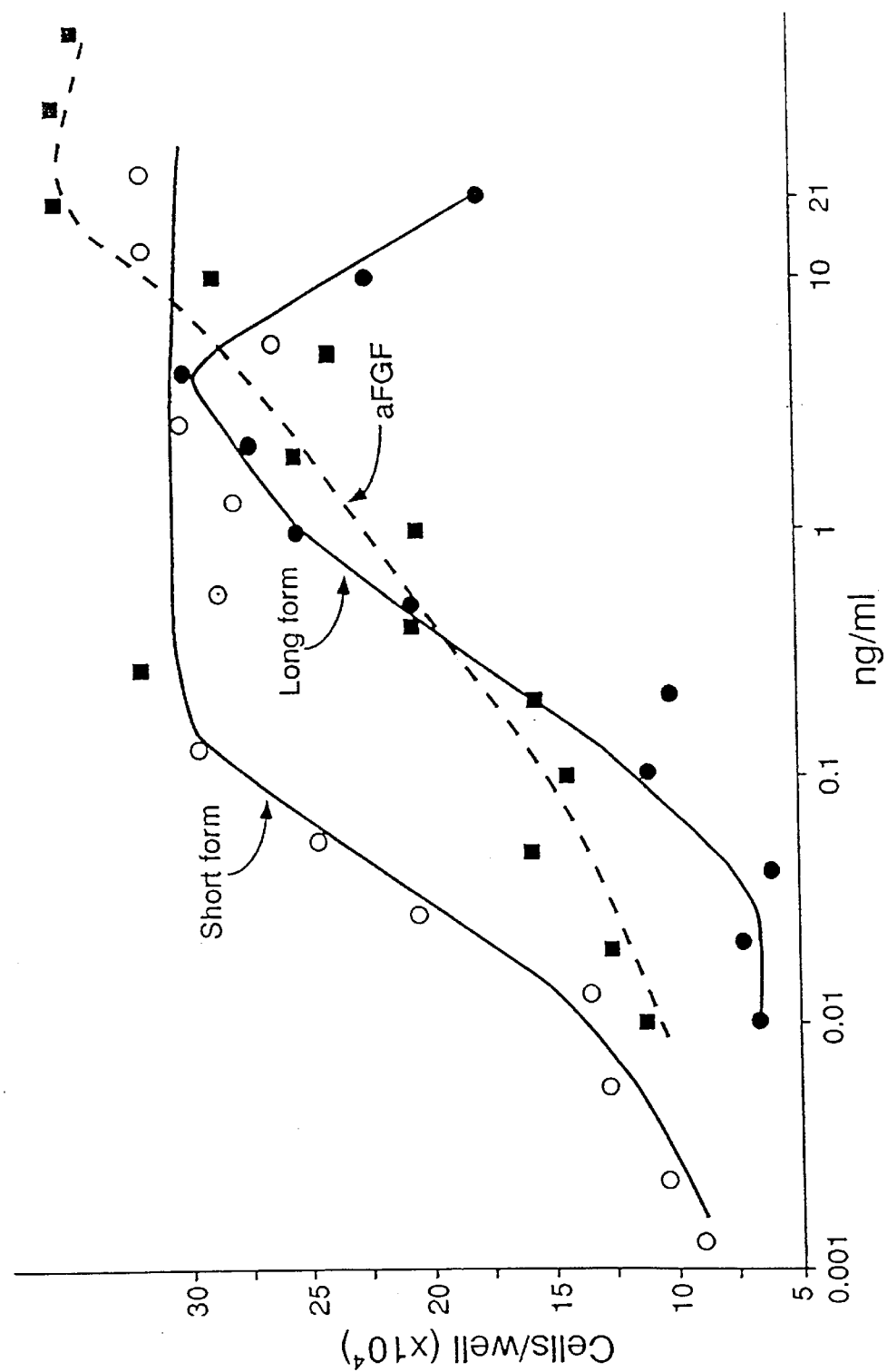
FIG. 4 compares the biological activity of the long, i.e., full-length rKGF, and the short, i.e., rKGF$_{des1-23}$, form of KGF versus aFGF on the cells of the Balb/Mk cell line. The figure legend for FIG. 4 is as follows: ○=KGF$_{des1-23}$, ●=KGF$_{163}$, and □=aFGF.

After five days in culture, the cells were trypsinized and the final cell density was determined using a Coulter® counter. The cells were released from the plates by replacing the culture medium with a solution containing 0.9% NaCl, 0.01 M sodium phosphate (pH 7.4), 0.05% trypsin, and 0.02% EDTA (STV). The cells were incubated in this solution for 5–10 minutes at 37° C., and then the stock culture medium was added to the cells. The cells were then counted using a Coulter® counter (Coulter Electronics, Hialeah, Fla., U.S.A.). Results shown in FIG. 4 demonstrates the effect of different dilutions of $rKGF_{des1-23}$ and $rKGF_{163}$ on Balb/Mk cells as compared to aFGF. The figure legend for FIG. 4 is as follows: ○=$KGF_{des1-23}$, ●=$KGF_{163}$, and □=aFGF.

The final cell density was graphed as a function of protein concentration. The protein concentration is graphed on a log scale. The protein concentration was determined by Bradford assay according to instructions accompanying the protein assay kit from BIORAD (Richmond, Calif., U.S.A.).

The $ED_{50}$ was calculated by (a), dividing in half the difference between the lowest and highest cell density value of the curve;and (b), determining from the graph what protein concentration corresponds to that cell density number obtained in (a). According to FIG. 4, the $ED_{50}$ for AFGF was found to be approximately 500 pg/ml, that for $rKGF_{163}$ was about 250 pg/ml, and that for $KGF_{des1-23}$ was about 24 pg/ml. The results of this assay demonstrate that $rKGF_{des1-23}$ was about 10-fold more active than $rKGF_{163}$.

The exact $ED_{50}$ for the proteins may vary from assay to assay, but the ratio of the activity between the long and short form of KGF is at least 2 fold, preferably, at least a 7-fold, more preferably, about 7–10 fold, even more preferably, at least 10 fold. Even a 50-fold difference in activity had been observed.

For example, the bioactivity assay was repeated with different or with the same preparations of $rKGF_{163}$ and $rKGF_{des1-23}$. The results of one of the assays showed that the $ED_{50}$ of $rKGF_{163}$ and $rKGF_{des1-23}$ were 600 pg/mi, and 80 pg/ml, respectively, about a 7-fold increase in activity. Another assay demonstrated a 50-fold difference between the long and short form of KGF. In this later assay, $KGF_{des1-23}$ exhibited an $ED_{50}$ of 30 pg/ml, and $KGF_{163}$ exhibited an $ED_{50}$ of 1500 pg/ml. In view of the fact that the last bioassay was done two (2) months after KGF isolation, the data suggest that upon storage, $KGF_{163}$ lost its bioactivity faster than $KGF_{des1-23}$.

D. Absence of KGF Bioactivity on ABAE or ACE Cells

KGF can be characterized by its lack of activity on vascular endothelial cells derived from large vessels ("ABAE") or capillary cells ("ACE") as compared with basic FGF ("bFGF"). Stock cultures of ABAE and ACE cells were grown and maintained in low calcium Dulbecco's modified Eagle medium supplemented with 10% bovine serum, 0.25 14g/ml fungizone, and 2 ng/ml bFGF. The cells were incubated at 37° C. with a 10% $CO_2$ concentration and 99% humidity.

In the mitogenic assay, either $10^4$ ABAE or $5 \times 10^3$ ACE cells were plated per well in 12-well plates in stock culture medium, as described is Gospodarowicz et al., *Proc. Nail. Acad. USA* 73: 4120–4124 (1976); Gospodarowicz et al,. *J. Cell. Physiol.* 127: 121–136 (1976); and Gospodarowicz et al., *Proc. Natl. Acad. USA* 86: 7311–7315 (1989). Ten microliter aliquots of the fractions to be tested were diluted into 1 ml of 0.2% (w/v) gelatin in phosphate buffered saline ("PBS"). Ten microliters of this dilution was added to cells seeded in 12-well cluster plates. A 10 µl aliquot of either the diluted purified rKGF medium containing fractions or 2 ng bFGF was added every other day.

After five days in culture, the cells were trypisinized and the final cell density was determined using a Coulter® counter. The cells were released from the plates by replacing the medium with a solution containing 0.9% NaCl, 0.01 M sodium phosphate (pH 7.4), 0.05% trypsin, and 0.02% EDTA (STV). The cells were incubated in this solution for 5–10 minutes at 37° C., and then the stock culture medium was added to the cells. The cells then were counted using a Coulter® counter (Coulter Electronics, Hialeah, Fla., U.S.A.).

Results shown in FIG. 5 demonstrates the lack of activity of both $rKGF_{163}$ and $rKGF_{des1-23}$ on ABAE cells and ACE cells, in contrast to bFGF. Similar observations were made using vascular smooth muscle cells, corneal endothelial cells, ovarian grandulosa cells, and BkH-21 fibroblasts. Although bFGF did stimulate the proliferation of these various cell types, neither $rKGF_{163}$ or $rKGF_{des1-23}$ had any bioactivity.

Example 6

Construction of a $KGF_{des1-23}$ Yeast Vector for Secretion by Yeast Cells

This example describes the construction of a yeast expression vector for secretion of $KGF_{des1}$_23 by transformed yeast cells in accordance with the present invention.

Specifically, the components of the expression vector construct: $KGF_{des1-23}$ coding sequence operably linked, at its 5' end, to a glyceraldehyde-3-phosphate dehydrogenase ("GAPDH") promoter and the coding sequence of the first 35 amino acid residues of the *Saccharomyces cerevisae* prepro α-factor leader sequence and, at its 3' end, to the *Saccharomyces cerevisae* α-factor terminator.

The fragments for this construct:

(1) a BamHI/Bpu1102I fragment containing the GAPDH promoter and the truncated prepro α-factor leader containing a functional signal peptide;

(2) a Bpu1102I /SalI fragment encoding $KGF_{dea1-23}$; and (3) a BamHI/SalI vector fragment of the yeast expression vector, pBS24.1, containing the α-factor terminator, leucine, and uracil yeast selectable markers, and 2 µ sequences as an origin of replication.

A. Construction of the BamHI/Bpu1102I Promoter/Leader Fragment

The source of the BamHI/Bpu1102I fragment: by PCR using pGAI7 as a template.

The plasmid pGAI7 is described in European Patent Application, Publication No. 324 274. This plasmid contains the same BamHI expression cassette as pYGAI7, which is available at the ATCC as Accession No. 67597. Plasmid pGAI7 contains approximately 400 bp GAPDH promoter fragment, as described in Travis et al,. *J. Biol. Chem.* 260:4384–4389 (1985), and the prepro α-factor leader sequence that encodes the N-terminal amino acid residues 1–35.

The primer for the PCR of BamHI/Bpu1102I promoter/leader fragment:

```
SEQ ID NO: 8 (sense)
       BamHI
5' GGTGGTGGATCCCCAGCTTAGTTCATAGGTCC 3'

SEQ ID NO: 10 (antisense)
    His Gln Asn Val Phe Arg Lys Ala Pro Ile Gln Ala*
5' GTG TTG GTT AAC GAA TCG CTT AGC CGG AAT TTG TGC 3'
                        Bpu1102I
```

*As encoded by the reverse complement of the primer, the peptide sequence is listed in the Sequence Listing as SEQ ID NO: 9.

Reagents for generating the BamHI/Bpu1102I fragments by PCR: 1 µl of each primer (100 pmoles/µl); 1 µl of the template, pGAI7 at ~500 µg/ml, and the following reagents from Perkin Elmer PCR kit (Norwalk, Conn.): 8 µl of dNTP (1.25 mM each of dATP, dTPP, dCTP, and dGTP), 10 µl of 10×buffer, 0.5 µl of Taq polymerase, and 63.5 µl of water. The temperature cycle for PCR: 94° C. for 1 minute, 37° C. for 2 minutes, and 72° C. for 3 minutes. Number of repetitions of this temperature cycle: 30. Purification of the PCR product of ~414 bp by gel purification, and by the use of a Geneclean kit by bio101, La Jolla, Calif. , U.S.A.

B. Construction of the Bpul/102I/SalI $KGF_{des1-23}$ Coding Sequence Fragment

The origin of the Bpu1102I/SalI $KGF_{des1-23}$ coding sequence fragment: by PCR using the pAcc/KGF baculovirus transfer vector described in Example 1 and 2.

The primers for PCR of the Bpu1102I/SalI $KGF_{des1-23}$ coding sequence:

```
SEQ ID NO: 12 (sense)
        Pro Ala Lys Arg Ser Tyr Asp Tyr Met Glu Gly Gly*
5' CCG CCG GCT AAG CGA AGT TAT GAT TAC ATG GAA GGA GGG
            Bpu1102I SEQ ID NO: 14 (antisense)
                   Stop Thr Ile Ala Met Pro Leu Phe His**
5' GGT GGT GTC GAC TTA AGT TAT TGC CAT AGG AAG AAA GTG 3'
           SalI
```

*The peptide sequence is listed as SEQ ID NO:11.
*As encoded by the reverse complement of the primer, and the peptide is listed as SEQ ID NO: 13.

Reagents for generating the Bpu102I/SalI KGF$_{des1-23}$ coding sequence by PCR: 1 µl of each primer (100 pmoles/µl), 1 µl of the template, pAcc/KGF, at 500 µg/ml, and the following reagents from Perkin Elmer PCR kit (Norwalk, Conn., U.S.A.): 8 µl of dNTP (1.25 mM each of dATP, dTTP, dCTP, dGTP), 10 µl of 10×buffer, 0.5 µl of Taq polymerase, and 63.5 µl of water. The temperature cycle for PCR: 94° C. for 1 minute, 37° C. for 2 minutes, and 72° C. for 3 minutes. Number of repetitions of this temperature cycle: 30. Purification of the PCR product of ~414 bp by gel purification, and by use of a Geneclean kit by bio101, La Jolla, Calif., U.S.A.

C. Construction of the BamHI/SalI Vector Fragment

The source of the BamHI/SalI vector fragment: by digesting the yeast expression vector pBS24.1 with BamHI and SalI. pBS24.1 is a yeast expression vector that is derived from pAB24. pBS24.1 contains the α-factor terminator; the 2µ sequences, as a yeast origin of replication; selectable markers for uracil and leucine in yeast; and an ampicillin resistance gene, effective in E. coli. This yeast expression vector also contains a human FGF coding sequence which can be excised by digestion with BamHI and SalI enzymes and isolating the larger vector fragment.

Plasmid pAB24 is a yeast shuttle vector that contains the complete 2µ sequence, as described in Broach, *Molecular Biology of the Yeast Saccharomyces*, Cold Spring Harbor Press 1:445 (1981) and pBR322 sequences. It also contains the yeast URA3 gene derived from plasmid YEp24, as described in Botstein, et al., *Gene* 8:17 (1979) and the yeast LEU$^{2d}$ gene derived from plasmid pCl/1, as described in European Patent Application, Publication No. 116 201. Plasmid pAB24 was constructed by digesting YEp24 with EcoRI and religating the vector to remove the partial 2µ sequences. The resulting plasmid, YEp24ΔR1, was linearized by digestion with ClaI and ligated with the complete 2µ plasmid which had been linearized with ClaI. The resulting plasmid, pCBou, was then digested with XbaI and the 8605 bp vector fragment was gel isolated. This isolated XbaI fragment was ligated with a 4460 bp XbaI fragment containing the Leu$^{2d}$ gene isolated from pCl/1; the orientation of the LEU$^{2d}$ gene is in the same direction as the URA3 gene. Insertion of the expression cassette was in the unique BamHI site of the pBR322 sequences, this interrupting the gene for bacterial resistance to tetracycline.

Plasmid pBS24 is a derivative of pAB24 as described. Plasmid pAB24 was digested with BamHI and SalI, which cut within the tetracycline gene of the pBR322 sequences, and gel purified. The vector was then ligated with a synthetic adapter of the following sequence which created new unique BglII and BamHI sites:

```
                                              (SEQ ID NO: 15)
           BglII              BamHI
5' -GATCAGATCTAAATTTCCCGGATCC-3'

TCTAGATTTAAAGGGCCTAGGAGCT  (SEQ ID NO:16)
  (BamHI)                     (SalI)
```

The resulting vector, pAB24ΔBL was then digested with BamHI and BglII and gel purified. The linearized vector was ligated with the BamHI cassette excised and purified from pSOD/env-5b to give pBS24. The cassette contains the hybrid ADH-2/GAPDH promoter and α-factor terminator with an NcoI-SalI insert of the SOD/env-5b fusion gene. The cassette is oriented in pBS24 such that the direction of transcription from the ADH-2/GAPDH promoter is in the opposite direction to that of the inactivated tetracycline gene of the pBR322 sequences.

pBS24.1 contains a BamHI/SalI fragment encoding the human FGF protein instead of the SOD/env-5b in pBS24, as described in U.S. Pat. No. 5,156,949. The relevant vector fragment of pBS24.1 is present in pBS24.1bBMP. pBS24.1bBMP is the same as pBS24.1 except is contains a BamHI/SalI bovine BMP expression cassette instead of the human FGF protein. The vector pBS24.1bBMP was deposited with the ATCC, Rockville, Md., U.S.A., on Jun. 1, 1989 under Accession no. 20949.

Example 7

Expression of rKGF$_{des1-23}$ by Yeast Cells

The procedure for expression of rKGF$_{des1-23}$ in accordance with the present invention:

The secretory expression vector: as described in Example 6.

Host for expression: *Saccharomyces cerevisae*.

Method of introducing the expression vector into host cells: by electroporation, as described in "Guide to Yeast Genetics & Molecular Biology," in *Methods in Enzymology*, Vol. 194 (Academic Press 1991).

Selection of transformants: on ura⁻ with 2% glucose medium.

Seed culture of transformants: overnight incubation in 1 ml of leu⁻ with 2% glucose medium at 30° C. in a shaking apparatus.

For production of rKGF$_{des1-23}$ expression: 20 ml culture seeded with the overnight culture in ura⁻ with 2% glucose medium, for approximately 72 hours.

Example 8

Construction of a KGF$_{des1-23}$ Yeast Vector for Intracellular Yeast Expression This example describes a procedure for construction of a yeast expression vector, for intracellular expression of the KGF$_{des1-23}$ by transformed yeast cells, in accordance with the present invention:

Specifically, the components of the expression vector: KGF$_{des1-23}$ coding sequence, a hybrid yeast promoter and an α-factor terminator.

The fragments for construction of this vector:
(1) BamHI/NcoI fragment containing the ADH2/GAPDH promoter;
(2) BspHI/SalI fragment encoding KGF$_{des1-23}$; and
(3) BamHI/SalI vector fragment of the yeast expression vector, pBS24.1, containing the *Saccharomyces cerevisae* α-factor terminator, leucine and uracil yeast selectable markers, and 2µ sequences as an origin of replication.

A. Construction of a KGF$_{des1-23}$ Coding Sequence

Construction of the BspHI/SalI KGF$_{des1-23}$ coding sequence fragment: by PCR using the pAcc/KGF baculovirus transfer vector, as described in Example 1 and 2.

The primers for PCR:

```
SEQ ID NO: 18 (sense)
            Met Ser Tyr Asp Tyr Met Glu Gly Gly*
5' GT TGT TTC ATG AGT TAT GAT TAC ATG GAA GGA GGG
          BspHI SEQ ID NO: 14 (antisense)
              Stop Thr Ile Ala Met Pro Leu Phe His**
5' GGT GGT GTC GAC TTA AGT TAT TGC CAT AGG AAG AAA GTG 3'
          SalI
```

*The peptide sequence is listed as SEQ ID NO: 17.
**As encoded by the reverse complement of the primer, and the peptide sequence is listed as SEQ ID NO: 12.

Reagents for construction of the BspHI SalI KGF$_{des1-23}$ coding sequence by PCR: 1 µl of each primer (100 pmoles/µl), 1 µl of the template, pGAI7, at ~500 µg/ml, and the following reagents from Perkin Elmer PCR kit (Norwalk, Conn.): 8 µl of dNTP (1.25 mM each of dATP, dTPP, dCTP, and dGTP), 10 µl of 10×buffer, 0.5 µl of Taq polymerase, and 63.5 µl of water. The temperature cycle for PCR: 94° C. for 1 minute, 37° C. for 2 minutes, and 72° C. for 3 minutes. Number of repetitions of the temperature cycle: 30. Purification of the PCR product of ~414 bp by gel purification, and by use of a Geneclean kit by bio101, La Jolla, Calif., U.S.A.

B. Construction of a BamHI/NcoI Promoter Fragment

The source of the BamHI/NcoI promoter fragment: by digestion of pSI3 containing a superoxidase dismutase (SOD)/insulin fusion yeast expression cassette comprising a BamHI/NcoI, ADH2/GAPDH hybrid promoter. to release a fragment of about 1366 bp containing the hybrid promoter sequences. pSI3 is a derivative of pYASIl, which was deposited with the ATCC, Rockville, Md., U.S.A, on Feb. 27, 1985, and assigned Accession no. 20745. The construction of pYASI1 is described in U.S. Pat. No. 4,751,180. pYASI1 contains the same BamHI/NcoI hybrid promoter fragment as pSI3.

C. Construction of the BamHI/SalI pBS24.1 Vector Fragment

Source of BamHI/SalI pBS24.1 vector fragment: by digestion of pBS24.1 with BamHI and SalI and isolation of the large vector fragment, as described in Example 6, section C.

Example 9

Intracellular Expression of rKGF$_{des1-23}$, by Yeast Cells

Procedure for intracellular expression of rKGF$_{des1-23}$ by yeast cells in accordance with the present invention:

Expression vector for intracellular expression in yeast cells: as described in Example 8.

Host cells for transformation: *Saccharomyces cerevisae*.

Method of introducing expression vector into host cells: by electroporation, was described in "Guide to Yeast Genetics & Molecular Biology," *Methods in Enzymology*, Vol. 194 (Academic Press, 1991).

Selection of transformants: on ura⁻ with 2% glucose medium.

Seed culture of transformants: overnight incubation in 1 ml of leu⁻ with 2% glucose medium at 30° C. in a shaking apparatus. Culture for production of rKGF$_{des1-23}$: a 20 ml culture seeded with the overnight culture in ura⁻ with 2% glucose medium for approximately 72 hours.

Deposit Information:
The following materials were deposited with the American Type Culture Collection:

| Virus Name | Deposit Date | Accession No. |
| --- | --- | --- |
| *Autographa californica* nuclearpolyhedrosis virus KGP-5 | June 17, 1993 | VR2411 |
| *Escherichia coli*, pYGAI7 | Dec. 29, 1987 | 67597 |
| *Saccharomyces cerevisae* pBS24.IbBMP | June 1, 1989 | 20949 |
| *Saccharomyces cerevisae*, 2150-2-3 pYASI1 | Feb. 27, 1985 | 20745 |

The above materials have been deposited with the American Type Culture Collection, Rockville, Md., under the accession numbers indicated. This deposit will be maintained under the terms of the Budapest Treaty on the International Recognition of the Deposit of Microorganisms for purposes of Patent Procedure. The deposits will be maintained for a period of 30 years following issuance of this patent, or for the enforceable life of the patent, whichever is greater. Upon issuance of the patent, the deposits will be available to the public from the ATCC without restriction.

These deposits are provided merely as convenience to those of skill in the art, and are not an admission that a deposit is required under 35 U.S.C. §112. The sequence of the polynucleotides contained within the deposited materials, as well as the amino acid sequence of the polypeptides encoded thereby, are incorporated herein by reference and are controlling in the event of any conflict with the written description of sequences herein. A license may be required to make, use, or sell the deposited materials, and no such license is granted hereby.

---

What is claimed:

1. An isolated polypeptide, wherein said potypeptide is a fragment of mature, full-length, human KGF having an amino acid sequence comprising at least the contiguous amino acid sequence of amino acids 24–163 of FIG. 1 (amino acids 55–194 of SEQ ID NO: 1), and further wherein said polypeptide exhibits an increase in bioactivity relative to mature, full-length, human KGF as determined by the Balb/MK bioactivity assay and specifically stimulates epithelial cell proliferation.

2. A composition comprising the polypeptide of claim 1 and a pharmaceutically acceptable vehicle.

* * * * *